United States Patent [19]

Schinazi et al.

[11] Patent Number: 6,020,369
[45] Date of Patent: Feb. 1, 2000

[54] METHOD COMPOSITIONS AND APPARATUS FOR TREATING AND PREVENTING RESPIRATORY VIRAL INFECTIONS

[76] Inventors: Raymond F. Schinazi, 1524 Regency Walk Dr., Decatur, Ga. 30033; Craig L. Hill, 2941 Cravey Dr., Atlanta, Ga. 30349

[21] Appl. No.: 09/111,275

[22] Filed: Jul. 7, 1998

Related U.S. Application Data

[60] Division of application No. 08/399,700, Mar. 3, 1995, Pat. No. 5,824,706, which is a continuation-in-part of application No. 08/312,561, Sep. 26, 1994, abandoned.

[51] Int. Cl.$^7$ ............ A01N 55/02; A01N 59/14; A01N 59/16; A01N 59/20
[52] U.S. Cl. ............ 514/492; 514/494; 514/499; 514/501; 514/502; 514/617; 514/630; 514/635; 514/639; 514/641; 514/646; 514/647; 514/648; 514/657
[58] Field of Search ............ 514/492, 494, 514/499, 501, 502, 617, 630, 635, 639, 641, 646, 647, 648, 657

[56] References Cited

U.S. PATENT DOCUMENTS

| | | |
|---|---|---|
| 4,547,369 | 10/1985 | Chermann et al. ............ 424/131 |
| 4,590,298 | 5/1986 | Che ............ 568/387 |
| 4,634,502 | 1/1987 | Callahan et al. ............ 200/23 |
| 4,681,933 | 7/1987 | Chu et al. ............ 536/27 |
| 4,759,929 | 7/1988 | Chermann et al. ............ 424/131 |
| 4,839,008 | 6/1989 | Hill ............ 204/157.15 |
| 4,841,039 | 6/1989 | Chu et al. ............ 536/29 |
| 4,864,041 | 9/1989 | Hill ............ 549/513 |
| 4,916,122 | 4/1990 | Chu et al. ............ 514/50 |
| 5,051,414 | 9/1991 | Domaille et al. ............ 514/184 |
| 5,077,279 | 12/1991 | Chu et al. ............ 514/49 |
| 5,084,445 | 1/1992 | Chu et al. ............ 514/49 |
| 5,093,134 | 3/1992 | Murrer et al. ............ 424/617 |
| 5,093,327 | 3/1992 | Domaille et al. ............ 514/184 |
| 5,512,305 | 4/1996 | Abrams et al. ............ 424/617 |

FOREIGN PATENT DOCUMENTS

| | | |
|---|---|---|
| 0 388 245 | 9/1990 | European Pat. Off. . |
| 0 390 365 | 10/1990 | European Pat. Off. . |
| 93/21934 | 11/1993 | WIPO . |
| 94/12192 | 6/1994 | WIPO . |
| 95/11033 | 4/1995 | WIPO . |
| 95/31202 | 11/1995 | WIPO . |

OTHER PUBLICATIONS

Rhule, J. T., et al., Chem Rev. vol. 98, No. 1, pp. 327–357, 1998.
B. Moskovitz et al, *Antimicrob. Agents and Chemoth.,* vol. 32, pp. 1300–1303 (1988).
C. Jasmin et al, *Biomedicine,* vol. 18, pp. 319–327 (1973).
C. Jasmin et al, *J. Natl. Cancer Inst.,* vol. 53, pp. 469–474 (1974).
J.-C. Chermann et al, *Biochem. Biophys. Res. Comm.,* vol. 65, pp. 1229–1235 (1975).
G. Werner et al, *J. gen. Virol.,* vol. 31, pp. 59–64 (1976).
D. Ablashi et al, *Eur. J. Cancer,* vol. 13, pp. 713–718 (1977).
H. Tsiang et al, *J. gen. Virol.,* vol. 40, pp. 665–668 (1978).
R. Kimberlin et al, *The Lancet,* pp. 591–592 (Sep. 15, 1979).
M. Michelon et al, *J. inorg. nucl. Chem.,* vol. 42, 1583–1586 (1980).
B. Schönfeld et al, *Z. Naturforsch,* vol. 30b, pp. 959–960 (1975).
C. Cibert et al, *Biochem. Biophys. Res. Comm.,* vol. 108, pp. 1424–1433 (1982).
N. Larnicol et al, *J. gen. Virol.,* vol. 55, pp. 17–23 (1981).
M. Herve et al, *Biochem. Biophys. Res. Comm.,* vol. 116, pp. 222–229 (1983).
R. Kimberlin et al, *Arch. Virol.* vol. 78, pp. 9–18 (1983).
F. Bussereau et al, *Ann. Virol.,* vol. 134 E, pp. 487–506 (1983).
M. Souyri–Caporale et al, *J. gen. Virol.,* vol. 65, pp. 831–835 (1984).
W. Rozenbaum et al, *The Lancet,* pp. 450–451 (Feb. 23, 1985).
R. Kimberlin et al, *Antimicrob. Agents Chemoth.,* vol. 30, pp. 409–413 (1986).
J. Blancou et al, Current Chemotherapy and Immunotherapy, *Proceedings of the 12th International Congress of Chemotherapy,* Italy, vol. 2, pp. 1070–1071 (1981).
Kirk–Othmer Encyclopedia of Chemical Technology, 4th Ed., vol. 1, pp. 670–685 (1991).
J. Fox, *ASM News,* vol. 52, pp. 12–16 (1986).
M. Pepin et al, *Arch. Virol.,* vol. 83, pp. 327–329 (1985).
D. Riesenberg, *JAMA,* vol. 254, pp. 2521–2529 (1985).
M. Michelon et al, *C. R. Acad. Sc. Paris,* vol. 274, pp. 209–212 (1972).
C. Bonissol, *C. R. Acad. Sc. Paris,* vol. 274, pp. 3030–3033 (1972).
T. Nemetschek et al, *J. Mol. Biol.,* vol. 133, pp. 67–83 (1979).
R. Schinazi et al, Selective Antiviral Activity of a Silicotungstate Heteropoly Acid Against HTLV3/LAV and Herpes Simplex Virus, presented at *26th ICAAC,* New Orleans, Louisiana (1986).
J. Blasecki, "Of Therapy, Toxicity and Tungstates: The anti–Retroviral Pharmacology of Polyoxometalates," in *Polyoxometalates,* Pope et al, Eds, Kluwer Academic Publishers, pp. 373–385 (1994).
M. Raynaud, *C.R. Acad. Sc. Paris.* vol. 272, pp. 347–348 (1971).
D. Dormont et al, *Cancer Detection and Prevention,* vol. 12, pp. 181–194 (1988).
W. Turner et al, *P.S.E.B.M.,* vol. 138, pp. 1030–1034 (1971).
M. Alizadeh et al, *J. Am. Chem. Soc.,* vol. 107, pp. 2662–2669, (1985).

(List continued on next page.)

*Primary Examiner*—Nathan M. Nutter
*Attorney, Agent, or Firm*—Sherry M. Knowles; Jacqueline Haley; King & Spalding

[57] ABSTRACT

Respiratory viral infections may be effectively prevented or treated by administering an aerosol spray comprising a polyoxometalate to the lungs.

12 Claims, 2 Drawing Sheets

OTHER PUBLICATIONS

R. Finke et al., *J. Am. Chem. Soc.,* vol. 103, pp. 1587–1589, (1981).
C. Brevard et al, *J. Am. Chem. Soc.,* vol. 105, pp. 7059–7063 (1983).
W. Knoth, *Inorg. Chem.,* vol. 25, pp. 1577–1584 (1986).
R. Finke et al, *Inorg. Chem.,* vol. 26, pp. 3886–3896 (1987).
S. Ikeda et al, *Antiviral Chem. Chemother.,* vol. 4(5), pp. 253–262 (1993).
R. Ruprecht et al, *Nature,* vol. 323, pp. 467–469 (1986).
Y. Take et al, *Antiviral Res.,* vol. 15, pp. 113–124 (1991).
D. Judd et al, *Antiviral Chem. Chemother.,* vol. 5(6), pp. 410–414 (1994).
L. Ni et al, *Antimicrob. Agents Chemother.,* vol. 38, pp. 504–510 (1994).
N. Yamamoto et al, *Mol. Pharmacol.,* vol. 42, pp. 1109–1117 (1992).
M. Fukuma et al, *Antiviral Res.,* vol. 16, pp. 327–339 (1991).
M. Cholewa et al, *Life Sciences,* vol. 54, pp. 1607–1612 (1994).
T.–C. Chou et al, *Adv. Enz. Regul.,* vol. 22, pp. 27–55 (1984).
M. Dabbabi et al, *J. Inorg. Nucl. Chem.,* vol. 38, pp. 1011–1014 (1976).
M. Droege, *J. Mol Catal.,* vol. 69, pp. 323–338 (1991).
D. Edlund et al, *Organomet,* vol. 7, pp. 1692–1704 (1988).
B. Ericksson et al, *Antimicrob. Agents Chemother.,* vol. 31, pp. 600–604 (1977).
R. Finke et al, *J. Am. Chem. Soc.,* vol. 106, pp. 7274–7277 (1984).
M. Fischl, *New England J. Med.,* vol. 317, pp. 185–191 (1987).
J. Groopman et al, *AIDS Res. Human Retro.,* vol. 3, pp. 71–85 (1987).
G. Hervé et al, *Inorg. Chem.,* vol. 16, pp. 2115–2117 (1977).
C. Hill et al, in *Advances in Chemotherapy of AIDS,* Diaso et al, Eds., Pergamon Press, New York, pp. 33–41 (1990).
C. Hill et al, *J. Med. Chem.,* vol. 33, pp. 2767–2772 (1990).
J. Horwitz et al, *J. Org. Chem.,* vol. 29, pp. 2076–2078 (1964).
M. Hosoya, *Antimicrob. Agents Chemother.,* vol. 35, pp. 2515–2520 (1991).
Kirk–Othmer Encyclopedia of Chemical Technology, 3rd Ed., vol. 21, pp. 466–483 (1983).
G. Kim et al, *J. Med. Chem.,* vol. 37, pp. 816–820 (1994).
C. Krieg et al, *Exptl. Cell. Res.,* vol. 116, pp. 21–29 (1978).
B. Larder et al, *Science,* vol. 243, pp. 1731–1734 (1989).
D. Lyon et al, *J. Am. Chem. Soc.,* vol. 113, pp. 7209–7221 (1991).
M. Pope, *Heteropoly and Isopoly Oxometalates,* Sringer–Verlag, Berlin, pp. 1–181, 1983.
J. McDougal et al, *J. Immun. Meth.,* vol. 76, pp. 171–183 (1985).
H. Mitsuya et al, *Proc. Natl. Acad. Sci. USA,* vol. 82, pp. 7096–7100 (1985).
H. Nishimura et al, *J. Gen. Virol.,* vol. 70, pp. 1653–1661 (1989).
W. Ostertag et al., *Proc. Natl. Acad. Sci. USA,* vol. 71, pp. 4980–4985 (1974).
Pauwels et al, *J. Virol. Meth.,* vol. 20, pp. 309–321 (1988).
D. Richman et al, *N.E.J. Med.,* vol. 317, pp. 192–197 (1987).
R. Schinazi et al, *Antimicrob. Agents Chemother.,* vol. 22. pp. 499–507 (1982).
S. Shigeta et al, *Antimicrob. Agents Chemother.,* vol. 36, pp. 435–439 (1992).
S. Shigeta et al, *Antiviral. Agents Chemother.,* vol. 3. pp. 171–177 (1992).
J. Sommadossi et al, *Antimicrob. Agents Chemother.,* vol. 31, pp. 452–454 (1987).
T. Spira et al, *J. Clin. Microbiol.,* vol. 25, pp. 97–99 (1987).
A. Tézé et al, *J. Inorg. Nucl. Chem.,* vol. 39, pp. 999–1002 (1977).
M. Weeks, *J. Med. Chem.,* vol. 35, pp. 1216–1221 (1992).
R. Yarchoan et al, *The Lancet,* pp. 575–580, (Mar. 15, 1986).
J. T. Rhule, *Chem. Rev.,* vol. 98, pp. 327–357 (1998).

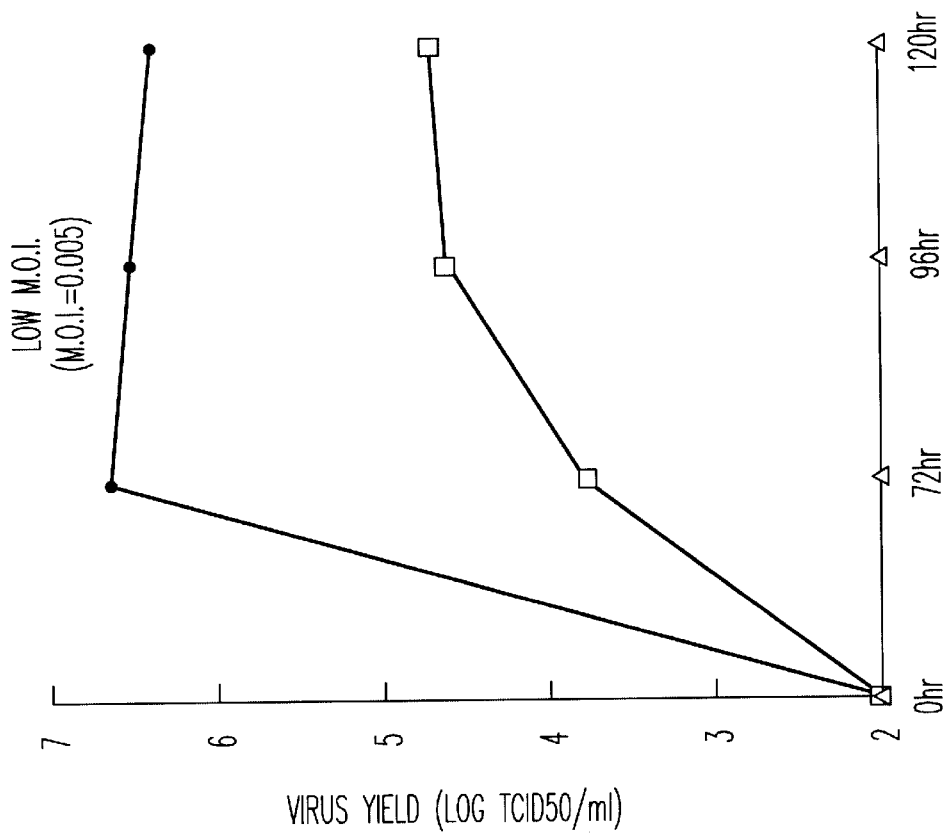
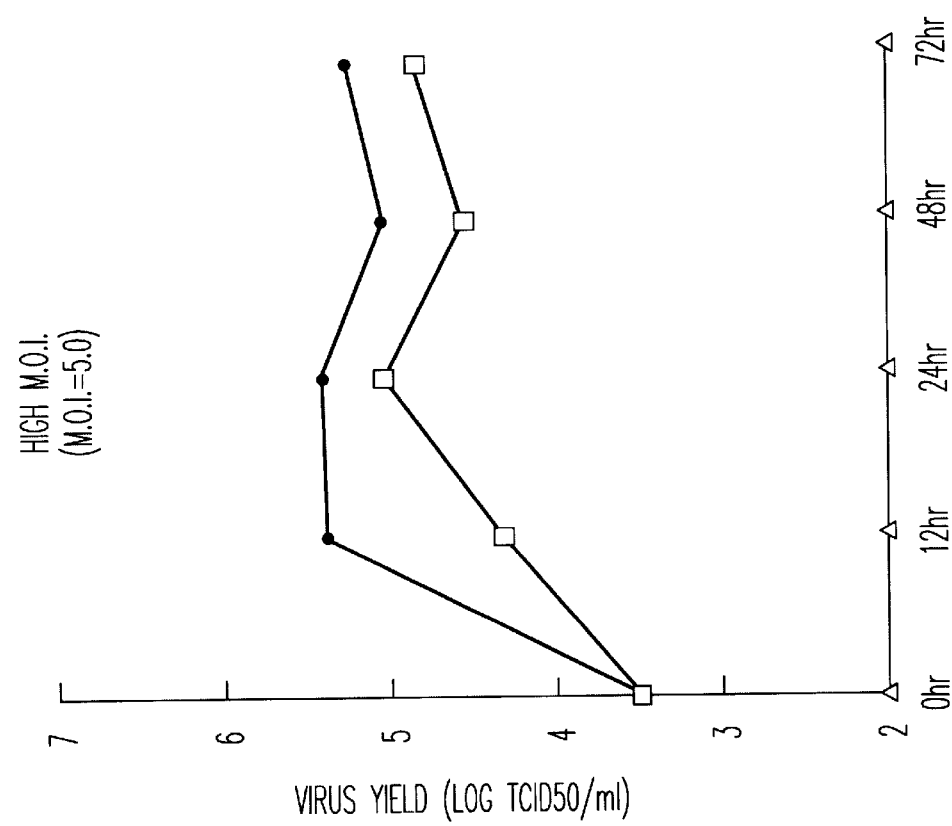

METHOD COMPOSITIONS AND APPARATUS FOR TREATING AND PREVENTING RESPIRATORY VIRAL INFECTIONS

This application is a Division of application Ser. No. 08/399,700 filed Mar. 3, 1995 and now U.S. Pat. No. 5,824,706, which is a continuation-in-part of application Ser. No. 08/312,561, filed Sep. 26, 1994, abandoned.

This invention was made with the assistance of U.S. Government funding under NIH Grant No. AI 32903. The U.S. Government may have some rights in this invention.

BACKGROUND OF THE INVENTION

1. Field of the Invention

The present invention relates to a method of treating respiratory viral infections, compositions useful for treating and/or preventing respiratory viral infections, and apparatus for delivering such compositions. The present invention also relates to methods of treating herpesvirus infection and hepadnavirus infection.

2. Discussion of the Background

Respiratory viral infections are an important cause of respiratory disease. Examples of such respiratory diseases arising from viral infection include influenza A, influenza B, and respiratory syncytial virus (RSV).

There are a number of drugs available for such respiratory viral infections, including ribavirin, amantadine, and rimantadine. However, none of these therapies are completely satisfactory. In particular, such drugs may be accompanied by side effects including nausea, hematological toxicity, and the development of resistant viruses.

Polyoxometalates are soluble inorganic cluster-like compounds formed principally of oxide anion and early transition metal cations. Some major polyoxometalate structural families are as follows: (1) the Keggin class (e.g., $\alpha\text{-SiW}_{12}O_{40}^{4-}$); (2) the Wells-Dawson class (e.g., $P_2W_{18}O_{62}^{6-}$); (3) fragments from these structures (e.g., $PW_{11}O_{39}^{7-}$); (4) the Keggin derived sandwich compounds (e.g., $K_{10}Fe_4(H_2O)_2(PW_9O_{34})_2$, code name, HS058); (5) the hexametalates or the Lindquist class (e.g., $W_6O_{19}^{2-}$), decatungstate ($W_{10}O_{32}^{4-}$); and (6) the Preyssler ion $[(NaP_5W_{30}O_{114})^{14-}]$ (Hill, C. L., et al, *J. Med. Chem*, vol. 33, pp. 2767–2772 (1990); Hill, C. L., et al, in *Advances in Chemotherapy of AIDS*, Diasio, R. B., et al, Eds, Pergamon Press, New York, pp. 33–41 (1990).

The potent and selective anti-human immunodeficiency virus type-1 (HIV-1) activity of polyoxometalates in infected human peripheral mononuclear (PBM) cells or cultured CD4+ T-cell lines has been reported by several workers. (Hill, C. L., et al, *J. Med. Chem*, vol. 33, pp. 2767–2772 (1990); Hill, C. L., et al, in *Advances in Chemotherapy of AIDS*, Diasio, R. B., et al, Eds, Pergamon Press, New York, pp. 33–41 (1990); Kim, G.-S., et al, *J. Med. Chem.*, vol. 37 (1994), Yamamoto, N. et al, *Mol. Pharmacol.*, vol. 42, pp. 1109–1117 (1992). Polyoxometalates have also been shown to be broadly inhibitory against retro-, myxo-, herpes-, toga-, rhabdo- and arenaviruses replications in vitro (Ikeda S. et al, *Antiviral Chem. Chemother.*, vol. 4, pp. 253–262 (1993); Yamamoto, N. et al, *Mol. Pharmacol.*, vol. 42, pp. 1109–1117 (1992). The mechanism of anti-HIV action may be attributed to inhibition of virus cell binding and inhibition of syncytium formation (Hill, C. L., et al, *J. Med. Chem*, vol. 33, pp. 2767–2772 (1990); Kim, G.-S. et al, Unpublished work; Take, Y., et al, *Antiviral Res.*, vol. 15, pp. 113–124 (1991). A similar mechanism of anti-viral action has also been suggested against influenza virus (FluV)-A and respiratory syncytial virus (RSV) (Ikeda S. et al, *Antiviral Chem. Chemother.*, vol. 4, pp. 253–262 (1993).

However, to date, there is no report of the treatment of respiratory viral infection by the administration of a polyoxometalate. Thus, there remains a need for a method of treating respiratory viral infections. There also remains a need for compositions and apparatus useful for treating respiratory viral infections. There also remains a need for treating human herpesvirus infections and hepadnavirus infections.

SUMMARY OF THE INVENTION

Accordingly, it is one object of the present invention to provide novel methods for treating respiratory viral infections.

It is another object of the present invention to provide novel methods for preventing respiratory viral infections.

It is another object of the present invention to provide novel compositions for treating respiratory viral infections.

It is another object of the present invention to provide novel compositions for preventing respiratory viral infections.

It is another object of the present invention to provide apparatus for dispensing such compositions.

It is another object of the present invention to provide novel methods for treating human herpesvirus infection.

It is another object of the present invention to provide novel methods for treating human hepadnavirus infection.

These and other objects, which will become apparent during the following detailed description, have been achieved by the inventors' discovery that administration of an effective amount of polyoxometalate is effective for the treatment and prevention of respiratory viral infection and that polyoxometalates may be conveniently administered to the lungs of an animal in the form of an aerosol spray. The inventors have also discovered that human herpesvirus infection and human hepadnavirus infection may be effectively treated by administering an effective amount of a polyoxometalate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1*a* and *b* show the inhibitory effects of HS-058 on virus yield in MDCK cells infected with FluV-A. Cells were infected with a multiplicity of infection (moi) of 5.0 (FIG. 1*a*), or 0.005 (FIG. 1*b*). cultures were treated with 4.4 $EC_{50}$ (6.0 μM) of HS-058 from 60 min before (Δ) or 90 min after (□) virus inoculation to the end of the experiment at 35° C. Control (●, mock treated) and experimental cultures were incubated at 37° C. for 90 min after virus inoculation, washed 3 times with maintenance medium, and then incubated at 35° C. with or without compound in medium.

DETAILED DESCRIPTION OF THE PREFERRED EMBODIMENTS

Figure 2:
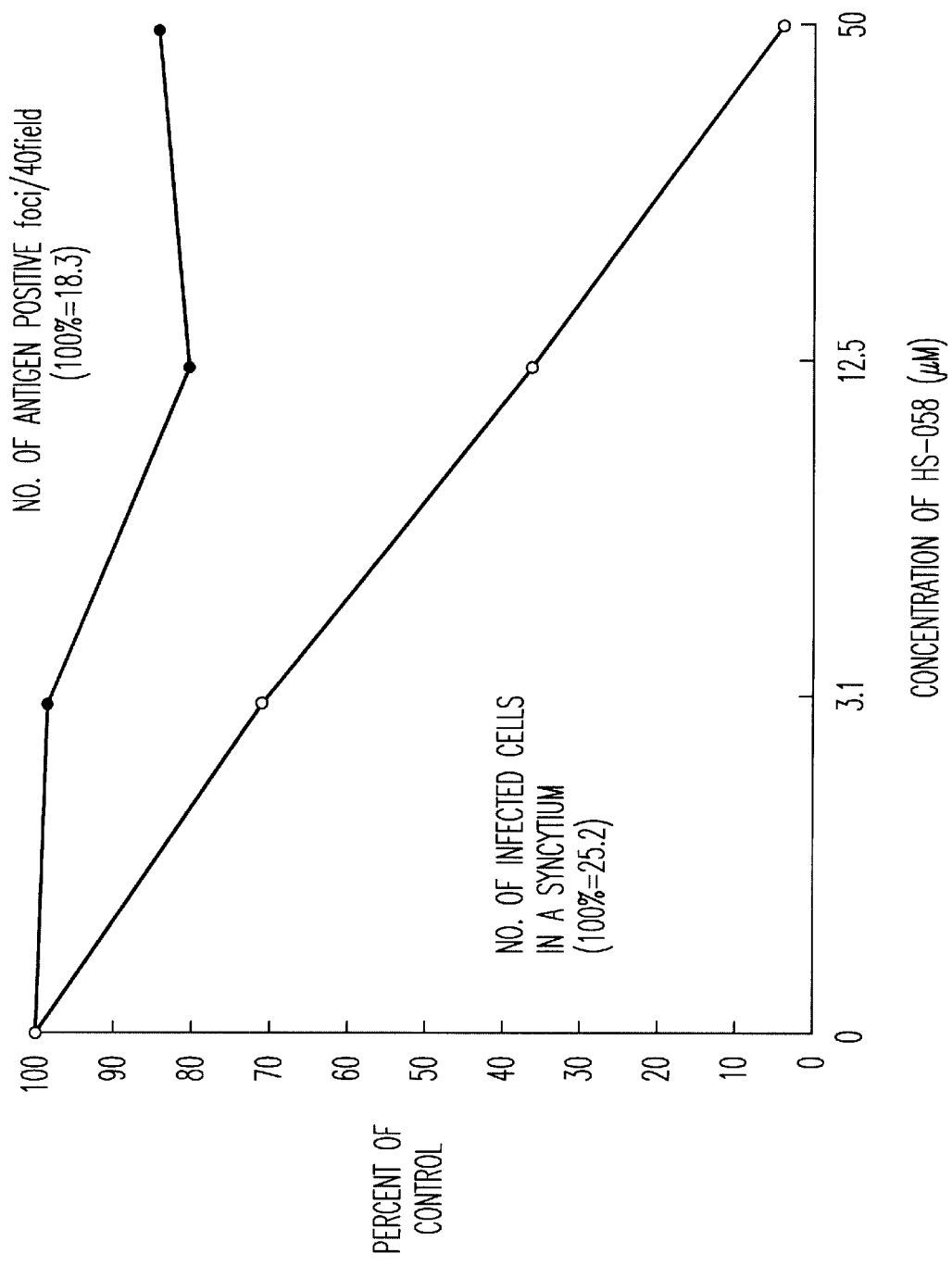
FIG. 2 shows the inhibitory effect of HS-058 against antigen synthesis and syncytium formation of RSV in HeLa cell monolayers. HeLa cells in Lab-Tec chamber were infected with 100 PFU/well of RSV and incubated at 37° C. After virus adsorption to cells by incubation for 90 min, infected cultures were treated with 1.6, 6, and 25 μM of HS-058 at 35° C. At 48 hr after infection, cells were fixed with acetone and stained with anti-RSV rabbit serum conjugated with fluorescein isothiocyanate. Cells were observed under a fluorescent microscope, and the number of antigen positive cells per 10 microscopic fields (●) and number of infected cells in one syncytium (○) were counted.

Thus, in a first embodiment, the present invention provides a method for treating respiratory viral infections by administering an effective amount of a polyoxometalate. In the context of the present invention, the term polyoxometalate includes compounds of the formulae:

| | |
|---|---|
| $(BW_{12}O_{40})^{5-}$ | (I) |
| $(W_{10}O_{32})^{4-}$ | (II) |
| $(P_2W_{18}O_{62})^{6-}$ | (III) |
| $PW_{11}O_{39}^{7-}$ | (IV) |
| $SiW_{11}O_{39}^{8-}$ | (V) |
| $HSiW_9O_{34}^{9-}$ | (VI) |
| $HPW_9O_{34}^{8-}$ | (VII) |
| $(TM)_4(PW_9O_{34})_2^{t-}$ | (VIII) |
| $(TM)_4(P_2W_{15}O_{56})_2^{t-}$ | (IX) |
| $[NaP_5W_{30}O_{110}]^{14-}$ | (X) |
| $(TM)_3(PW_9O_{34})_2^{12-}$ | (XI) |
| $P_2W_{18}O_6^{6-}$ | (XII) | wherein TM is a divalent or trivalent transition metal ion, such as $Mn^{+2}$, $Fe^{+2}$, $Fe^{+3}$, $Co^{+2}$, $Co^{+3}$, $Ni^{+2}$, $Cu^{+2}$ and $Zn^{+2}$, and wherein t is the valence of the anion which varies with the valency of TM;

$$[A_xW_yNb_aO_b]^{z-} \quad (XII)$$

in which A is one or more element selected from P, Si or Ge and x is zero or an integer from 1 to 40, y is an integer from 1 to 10, a is an integer from 1 to 8, b is an integer from 15 to 150, and z is an integer dependent upon the nature and oxidation state of element A, and their aqua complexes and active fragments.

In the context of the anions of formula (XIV), preferred ions are those in which element A is selected from one or more of H, P, Ge and Si. Preferably, when x=0, y=6–a, a is an integer from 1 to 5 and b=19; when A=Si or Ge, x=2, y=18, a=6 and b=77, and when A=P, x=2 or 4, y=12, 15, 17 or 30, a=1, 3 or 6 and b=62 or 123. The skilled artisan will readily appreciate that a molecule/ionic structure does not exist for every value of each integer in the above formula; examples of active ingredients will be given hereafter.

Obviously, these anions will be administered in the form of a pharmaceutically acceptable salt containing one or more of cations. The identity of the cation or cations is not particularly limited. Examples of suitable cations include $H^+$, $K^+$, $Na^+$, $NH_4^+$, mono-, di-, tri, or tetra-$(C_{1-4})$-alkylammonium, mono, di, tri, or tetra-$(C_{2-4})$-alkanolammonium, monocationic naturally-occurring amino acids (such as histidinium, argininium, or lysinium), oligo- or polypeptides containing one or more protonated basic amino acid residues, or any other common mono- or dication.

Specific examples of the polyoxometalates which may be used in the present invention are given in Table 1.

TABLE 1

CODE NUMBERS AND CHEMICAL FORMULAE OF POLYOXOMETALATES

| CODE NUMBER | FORMULAE | STRUCTURAL FAMILY |
|---|---|---|
| HS-003 | $[(NMP)_2H]_3PW_{12}O_{40}{}^a$ | |
| HS-004 | $[(DMA)_2H]_3PMo_{12}O_{40}{}^b$ | |
| HS-005 (HPA-23) | $(NH_4)_{17}Na[NaSb_9W_{21}O_{86}]$ | Inorganic Cryptate |
| HS-006 | a- and b-$H_5BW_{12}O_{40}(BT)$ | |
| HS-007 | a- and b-$H_6ZnW_{12}O_{40}$ | |
| HS-009 | a- and b-$H_6P_2W_{18}O_{62}$ | |
| HS-010 | α-$(NH_4)_6P_2W_{18}O_{62}$ | Wells Dawson |
| HS-011 | $K_{10}Cu_4(H_2O)_2(PW_9O_{34})_2 \cdot 20H_2O$ | |
| HS-012 | $K_{10}Co_4(H_2O)_2(PW_9O_{34})_2 \cdot 20H_2O$ | |
| HS-013 | $Na_7PW_{11}O_{39}$ | |
| HS-013A | $Na_7PW_{11}O_{39} \cdot 20H_2O + 2\ C_6H_5P(O)(OH)_2$ | |
| HS-014 | $(n-Bu_4N)_4H_3PW_{11}O_{39}$ | |
| HS-015 | b-$Na_8HPW_9O_{34}$ | |
| HS-016 | $(n-Bu_4N)_3PMoW_{11}O_{39}$ | |
| HS-017 | a-$[(nBu)_4N]_4Mo_8O_{26}$ | |
| HS-018 | $(n-Bu_4N)_2W_6O_{19}$ | |
| HS-019 | $(n-Bu_4N)_2Mo_6O_{19}$ | |
| HS-020 | a-$(NH_4)_nH_{(4-n)}SiW_{12}O_{40}$ | |
| NS-021 | a-$(NH_4)_nH_{(5-n)}BW_{12}O_{40}$ | |
| HS-022 | a-$K_5BW_{12}O_{40}$ | |
| HS-023 | $K_4W_4O_{10}(O_2)6$ | |
| HS-024 | b-$Na_9HSiW_9O_{34}$ | |
| HS-025 | $Na_6H_2W_{12}O_{40}$ | |
| HS-026 | $(NH_4)_{14}[NaP_5W_{30}O_{110}]$ | Preyssler |
| HS-027 | a-$(NH_4)_5BW_{12}O_{40}$ | |
| HS-028 | a-$Na_5BW_{12}O_{40}$ | |
| HS-029 | $(NH_4)_4W_{10}O_{32}$ | |
| HS-030 | $(Me_4N)_4W_{10}O_{32}$ | |
| HS-031 | $(HISH^+)_nH_{(5-n)}BW_{12}O_{40}{}^c$ | |
| HS-032 | $(LYSH^+)_nH_{(5-n)}BW_{12}O_{40}{}^d$ | |
| HS-033 | $(ARGH^+)_nH_{(5-n)}BW_{12}O_{40}{}^c$ | |
| HS-034 | $(HISH^+)_nH_{(4-n)}SiW_{12}O_{40}$ | |
| HS-035 | $(LYSH^+)_nH_{(4-n)}SiW_{12}O_{40}$ | |
| HS-036 | $(ARGH^+)_nH_{(4-n)}SiW_{12}O_{40}$ | |

TABLE 1-continued

CODE NUMBERS AND CHEMICAL FORMULAE OF POLYOXOMETALATES

| CODE NUMBER | FORMULAE | STRUCTURAL FAMILY |
|---|---|---|
| HS-037 | a-$K_8SiW_{11}O_{39}$ | |
| HS-037A | a-$K_8SiW_{11}O_{39}$ | |
| HS-038 | $K_{10}(H_2W_{12}O_{42})$ | |
| HS-039 | $K_{12}Ni_3(II)(PW_9O_{34})_2 \cdot nH_2O$ | |
| HS-040 | $(NH_4)_{10}Co_4(II)(PW_9O_{34})_2 \cdot nH_2O$ | |
| HS-041 | $K_{12}Pd_3(II)(PW_9O_{34})_2 \cdot nH_2O$ | |
| HS-042 | $Na_{12}P_2W_{15}O_{56} \cdot 18H_2O$ | Lacunary (Defect) |
| HS-043 | $Na_{16}Cu_4(H_2O)_2(P_2W_{15}O_{56})_2 \cdot nH_2O$ | |
| HS-044 | $Na_{16}Zn_4(H_2O)_2(P_2W_{15}O_{56})_2 \cdot nH_2O$ | |
| HS-045 | $Na_{16}Co_4(H_2O)_2(P_2W_{15}O_{56})_2 \cdot nH_2O$ | |
| HS-052 | $Na_{16}Ni_4(H_2O)_2(P_2W_{15}O_{56})_2 \cdot nH_2O$ | Wells-Dawson Sandwich |
| HS-053 | $Na_{16}Mn_4(H_2O)_2(P_2W_{15}O_{56})_2 \cdot nH_2O$ | Wells-Dawson Sandwich |
| HS-054 | $Na_{16}Fe_4(H_2O)_2(P_2W_{15}O_{56})_2 \cdot nH_2O$ | Wells-Dawson Sandwich |
| HS-055 | $K_{10}Zn_4(H_2O)_2(PW_9O_{34})_2 \cdot 20H_2O$ | Keggin Sandwich |
| HS-056 | $K_{10}Ni_4(H_2O)_2(PW_9O_{34})_2 \cdot nH_2O$ | Keggin Sandwich |
| HS-057 | $K_{10}Mn_4(H_2O)_2(PW_9O_{34})_2 \cdot nH_2O$ | Keggin Sandwich |
| HS-058 | $K_{10}Fe_4(H_2O)_2(PW_9O_{34})_2 \cdot nH_2O$ | Keggin Sandwich |
| HS-059 | $K_{12}Cu_3(PW_9O_{34})_2 \cdot nH_2O$ | |
| HS-060 | $K_{12}(CoH_2O)_3(PW_9O_{34})_2 \cdot nH_2O$ | |
| HS-061 | $K_{12}Zn_3(PW_9O_{34})_2 \cdot 15H_2O$ | |
| HS-062 | $K_{12}Mn_3(PW_9O_{34})_2 \cdot 15H_2O$ | |
| HS-063 | $K_{12}Fe_3(PW_9O_{34})_2 \cdot 25H_2O$ | |
| HS-064 | $(ARGH^+)_{10}(NH_4)_7Na[NaSb_9W_{21}O_{86}]$ | |
| HS-065 | $(ARGH^+)_5HW_{11}O_{39} \cdot 17H_2O$ | |
| HS-066 | $K_7Ti_2W_{10}O_{40}$ | |
| HS-067 | $[(CH_3)_4N]_7Ti_2W_{10}O_{40}$ | |
| HS-068 | $Cs_7Ti_2W_{10}O_{40}$ | |
| HS-069 | $[HISH^+]_7Ti_2W_{10}O_{40}$ | |
| HS-070 | $(LYSH^+)_nNa_{7-n}PTi_2W_{10}O_{40}$ | |
| HS-071 | $(ARGH^+)_nNa_{7-n}PTi_2W_{10}O_{40}$ | |
| HS-072 | $Cs_4[SiW_{11}O_{39} \cdot O(SiCH_2CH_2C(O)OCH_3)_2]_4$— | |
| HS-073 | $[TBA]_3H_3V_{10}O_{28}{}^f$ | |
| HS-074 | $K_7HNb_6O_{19} \cdot 13H_2O$ | |
| HS-076 | $[(CH_3)_4N^+]_4SiW_{11}O_{39}$—$O(SiCH_2CH_2C(O)OCH_3)_2$ | |
| HS-077 | $[(CH_3)_4N^+]_4PW_{11}O_{39}$—$(SiCH_2CH_2CN)$ | |
| HS-078 | $[(CH_3)_4N^+]_4PW_{11}O_{39}$—$(SiCH_2CH_2Cl)$ | |
| HS-079 | $[(CH_3)_4N^+]_4PW_{11}O_{39}$—$(SiCH=CH_2)$ | |
| HS-080 | $Cs_4[SiW_{11}O_{39}$—$(SiCH_2CH_2CN)_2]$ | |
| HS-081 | $Cs_4[SiW_{11}O_{39}$—$(SiCH_2CH_2Cl)_2]$ | |
| HS-082 | $Cs_4[SiW_{11}O_{39}$—$(SiCH=CH_2)_2]$ | |
| HS-083 | $[(CH_3)_4N^+]_4SiW_{11}O_{39}O(SiCH_2CH_2CH_2CH_2CH_2CH_3)_2$ | Organic Derviatized |
| HS-084 | $[(CH_3)_4N^+]_4SiW_{11}O_{39}$—$O(SiCH_2CH_2CH_2Cl)_2$ | |
| HS-085 | $[(CH_3)_4N^+]_4SiW_{11}O_{39}$—$O(SiCH_2CH_2CH_2CN)_2$ | |
| HS-086 | $[(CH_3)_4N^+]SiW_{11}O_{39}$—$O(SiCH=CH_2)_2$ | |
| HS-087 | $[(CH_2)_4N^+]SiW_{11}O_{39}$—$O(SiC(CH_3)3)_2$ | |
| HS-088 | $[(CH_3)_4N^+]SiW_{11}O_{39}$—$O(SiCH_2CH(CH_3)_2)_2$ | |
| HS-089 | $[(CH_3)_4N^+]_3PW_{11}O_{39}O(SiCH_2CH_2COOCH_3)_2$ | Organic Derivatized |
| HS-090 | $K_5Mn(II)PW_{11}O_{39}$—$nH_2O$ | |
| HS-091 | $K_8Mn(II)P_2W_{17}O_{61} \cdot nH_2O$ | Transition Metal Substituted Polyoxmetalate |
| HS-092 | $K_6Mn(II)SiW_{11}O_{39} \cdot nH_2O$ | |
| HS-093 | $K_5PW_{11}O_{39}(SiMe_2) \cdot nH_2O$ | |
| HS-094 | $K_3PW_{11}O_{41}(PPh)_2 \cdot xH_2O$ | |
| HS-095 | $Na_3PW_{11}O_{41}(PPh)_2 \cdot xH_2O$ | |
| HS-096 | $K_5PTiW_{11}O_{40}$ | |
| HS-097 | $Cs_5PTiW_{11}O_{39}$ | |
| HS-098 | $K_6SiW_{11}O_{39}(SiMe_2) \cdot nH_2O$ | |
| HS-099 | $K_3PW_{11}O_{41}(PFt)_2 \cdot nH_2O$ | |
| HS-100 | $KsiW_{11}O_{39}[SiPh(t-Bu)] \cdot nH_2O$ | |
| HS-101 | $K_6SiW_{11}O_{39}(SiPh_2) \cdot nH_2O$ | |
| HS-102 | $K_7SiW_9Nb_3O_{40} \cdot nH_2O$ | |
| HS-103 | $Cs_7SiW_9Nb_3O_{40} \cdot nH_2O$ | |
| HS-104 | $Cs_8Si_2W_{18}Nb_6O_{77} \cdot nH_2O$ | |
| HS-105 | $(Me_3NH)_7SiW_9Nb_3O_{40} \cdot nH_2O$ | Substituted Keggin |
| HS-107 | $(CN_3H_6)_7SiW_9Nb_3O_{40} \cdot nH_2O$ | |
| HS-108 | $(CN_3H_6)_8Si_2W_{18}Nb_6O_{77} \cdot nH_2O$ | |
| HS-109 | $Rb_7SiW_9Nb_3O_{40} \cdot nH_2O$ | |
| HS-110 | $Rb_8Si_2W_{18}Nb_6O_{77} \cdot nH_2O$ | |
| HS-111 | $K_8Si_2W_{18}Nb_6O_{77} \cdot nH_2O$ | |
| HS-112 | $K_6P_2Mo_{18}O_{62} \cdot nH_2O$ | |
| HS-113 | $(C_5H_5N)_7HSi_2W_{18}Nb_6O_{77} \cdot nH_2O$ | |
| HS-114 | $(C_5H_5N)_7SiW_9Nb_3O_{40} \cdot nH_2O$ | |
| HS-115 | $(ARGH^+)_8SiW_{18}Nb_6O_{77} \cdot 18H_2O$ | |
| HS-116 | $(LYSH^+)_7KSiW_{18}Nb_6O_{77} \cdot 18H_2O$ | |

TABLE 1-continued

CODE NUMBERS AND CHEMICAL FORMULAE OF POLYOXOMETALATES

| CODE NUMBER | FORMULAE | STRUCTURAL FAMILY |
|---|---|---|
| HS-117 | $(HISH^+)_6K_2SiW_{18}Nb_6O_{77} \cdot 18H_2O$ | |
| HS-118a | $H_8Si_2W_{18}Nb_6O_{77} \cdot nH_2O$ (2 batches) | |
| HS-119 | $[(CH_3)_4N^+]_4SiW_{11}O_{39}\text{—}O(SiCH_2CH_3)_2$ | |
| HS-120 | $[(CH_3)_4N^+]_4SiW_{11}O_{39}\text{—}O(SiCH_3)_2$ | |
| HS-121 | $[(CH_3)_4N^+]_4SiW_{11}O_{39}\text{—}O(SiC_{16}H_{33})_2$ | |
| HS-122 | $Li_7HSi_2W_{18}Nb_6O_{77}$ | |
| HS-123 | $Li_9P_2V_3Me_3W_{12}O_{62}$ | |
| HS-124 | $Cs_9P_2V_3MeW_{12}O_{62}$ | |
| HS-125 | $Cs_{12}P_2V_3W_{12}O_{62}$ | |
| HS-126 | $K_4H_2PV_4W_8O_{40}$ | |
| HS-127 | $Na_{12}P_4W_{14}O_{58}$ | |
| HS-128 | $Na_{14}H_6P_6W_{18}O_{79}$ | |
| HS-129 | $a\text{-}K_5(NbO_2)SiW_{11}O_{39}$ | |
| HS-130 | $K_5(TaO_2)SiW_{11}O_{39}$ | |
| HS-131 | $(Me_3NH)_5(NbO_2)SiW_{11}O_{39}$ | Keggin Peroxo |
| HS-132 | $(Me_3NH)_5NbSiW_{11}O_{40}$ | Substituted Keggin |
| HS-133 | $(Me_3NH)_5(TaO_2)SiW_{11}O_{39}$ | Keggin Peroxo |
| HS-134 | $K_4(NbO_2)PW_{11}O_{39}$ | |
| HS-135 | $K_7(NbO_2)P_2W_{12}O_{61}$ | |
| HS-136 | $(Me_3NH)_7(NbO_2)_3SiW_9O_{37}$ | Keggin Peroxo |
| HS-137 | $Cs_7(NbO_2)_3SiW_9O_{37}$ | |
| HS-138 | $K_6(NbO_2)_3PW_9O_{37}$ | |
| HS-139 | $Na_{10}(H_2W_{12}O_{42})$ | |
| HS-140 | $K_4NbPW_{11}O_{40}$ | |
| HS-141 | $(Me_3NH)_4NbPW_{11}O_{40}$ | |
| HS-142 | $K_5NbSiW_{11}O_{40}$ | |
| HS-143 | $K_5TaSiW_{11}O_{40}$ | |
| HS-144 | $(Me_3NH)_5TaSiW_{11}O_{40}$ | Substituted Keggin |
| HS-145 | $K_6Nb_3PW_9O_{40}$ | |
| HS-146 | $K_7NbP_2W_{17}O_{62}$ | Wells-Dawson |
| HS-147 | $K_7(TiO_2)_2PW_{10}O_{38}$ | |
| HS-148 | $K_7(TaO_2)_3SiW_9O_{37}$ | |
| HS-149 | $K_7Ta_3SiW_9O_{40}$ | |
| HS-150 | $K_6(TaO_2)_3PW_9O_{37}$ | |
| HS-151 | $K_6Ta_3PW_9O_{40}$ | |
| HS-152 | $K_8Co_2W_{11}O_{39}$ | |
| HS-153 | $H_2(Me_4N)_4(EtSi)_2C0W_{11}O_{40}$ | |
| HS-154 | $H_2(Me_4N)_4(iso\text{-}C_4H_9Si)_2CoW_{11}O_{40}$ | |
| HS-155 | $K_9(NbO_2)_3P_2W_{15}O_{59}$ | |
| HS-156 | $K_9Nb_3P_2W_{15}O_{62}$ | |
| HS-157 | $K_{12}(NbO_2)_6P_2W_{12}O_{56}$ | Wells-Dawson Peroxo |
| HS-158 | $K_{12}Nb_6P_2W_{12}O_{62}$ | Wells-Dawson |
| HS-159 | $a_2\text{-}K_{10}P_2W_{17}O_{61}$ | |
| HS-160 | $K_6Fe(III)Nb_3P_2W_{15}O_{62}$ | |
| HS-161 | $K_7Zn(II)Nb_3P_2W_{15}O_{62}$ | |
| JM-1574 | $(NH_4)_6[a\text{-}P_2W_{18}O_{62}] \cdot nH_2O$ | |
| JM-1591 | $K_{12}[H_2P_2W_{12}O_{48}] \cdot 24H_2O$ | |
| JM-1591A | $K_{12}[H_2P_2W_{12}O_{48}] \cdot 24H_2O$ | |
| JM-1605 | $K_2Na_{15}H_{45}(PtMo_6O_{24})_8 \cdot 8H_2O$ | |
| JM-1638 | $K_8[a_2\text{-}P_2W_{17}MoO_{62}] \cdot nH_2O$ | |
| JM-1809A | $KHP_2V_3W_{15}O_{62} \cdot 34H_2O$ | |
| JM-1819 | $K_6[P_2W_{12}Nb_6O_{62}] \cdot 24H_2O$ | |
| JM-1827 | $Na_6[V_{10}O_{28}] \cdot 18H_2O$ | |
| JM-1832 | $(Guanidinium)_8H[PV_{14}O_{62}] \cdot 3H_2O$ | |
| JM-1835 | $K_8H[PV_{14}O_{62}]$ | |
| JM-1855 | $Na_7[MnV_{13}O_{38}] \cdot 18H_2O$ | |
| JM-2766 | $K_6[BW_{11}O_{39}Ga(OH_2)] \cdot 13H_2O$ | |
| JM-2768 | $K_7H[Nb_6O_{19}] \cdot 13H_2O$ | |
| JM-2768A | $K_7H[Nb_6O_{19}] \cdot 13H_2O$ | |
| JM-2775 | $[MeN/Na/K]_4[Nb_2W_4O_{19}]$ | |
| JM-2776 | $[Me_4N]_9[P_2W_{15}Nb_3P_{62}]$ | |
| JM-2799 | $[Me_4N]_{15}[HP_4W_{30}Nb_6O_{123}] \cdot 16H_2O$ | |
| JM-2799A | $[Me_4N]_{15}[HP_4W_{30}Nb_6O_{123}] \cdot 16H_2O$ | |
| JM-2800 | $[Na/K]_6Nb_4W_2O_{19}]$ | |
| JM-2801 | $[Me_4N/Na/K]_5[Nb_3W_3O_{19}] \cdot 6H_2O$ | |
| JM-2801A | $[Me_4N/Na/K]_5[Nb_3W_3O_{19}] \cdot 6H_2O$ | |
| JM-2802 | $[Me_5CpPh]_4V_6O_{19}]$ | |
| JM-2815 | $K_5[CpTiSiW_{11}O_{39}] \cdot 12H_2O$ | |
| JM-2840 | $b_2\text{-}K_8[SiW_{11}O_{39}] \cdot 14H_2O$ | |
| JM-2841 | $a\text{-}K_8[SiW_{10}O_{36}] \cdot 12H_2O$ | |
| JM-2842 | $Cs_7Na_2[PW_{10}O_{37}] \cdot 8H_2O$ | |
| JM-2843 | $Cs_6[P_2W_5O_{23}] \cdot 7(½)H_2O$ | |
| JM-2844 | $g\text{-}Cs_7[PW_{10}O_{36}] \cdot 7H_2O$ | |
| JM-2869 | $K_5[SiNbW_{11}O_{40}] \cdot 7H_2O$ | |

TABLE 1-continued

CODE NUMBERS AND CHEMICAL FORMULAE OF POLYOXOMETALATES

| CODE NUMBER | FORMULAE | STRUCTURAL FAMILY |
|---|---|---|
| JM-2870 | $K_4[PNbW_{11}O_{40}].12H_2O$ | |
| JM-2871 | $Na_6[Nb_4W_2O_{19}].13H_2O$ | |
| JM-2871A | $Na_6[Nb_4W_2O_{19}].20H_2O$ | |
| JM-2872 | $K_6[Nb_4W_2O_{19}].7H_2O$ | |
| JM-2873 | $K_4[V_2W_4O_{19}].3.5H_2O$ | |
| JM-2874 | $Na_5[V_3W_3O_{19}].12H_2O$ | |
| JM-2875 | $K_6[PV_3W_9O_{40}].14H_2O$ | |
| JM-2876 | $Na_9[A-b-GeW_9O_{34}].8H_2O$ | |
| JM-2877 | $Na_{10}[A-a-GeW_9O_{34}].9H_2O$ | |
| JM-2878 | $K_7[BV_2W_{10}O_{40}].6H_2O$ | |
| JM-2879 | $Na_5[CH_3Sn(Nb_6O_{19})].10H_2O$ | |
| JM-2879A | $Na_5[CH_3Sn(Nb_6O_{19})].10H_2O$ | |
| JM-2881 | $Na_8[Pt(P(m-SO_3Ph)_3)_3Cl].3H_2O$ | |
| JM-2882 | $Na_3[P(m-SO_3Ph)_3].H_2O$ | |
| JM-2919 | $(Me_3NH)_{10}(H)[Si_2(ZrOH)_3W_{18}O_{68}].10H_2O$ | |
| JM-2919A | $(Me_3NH)_{10}(H)[Si_2(ZrOH)_3W_{18}O_{68}].10H_2O$ | |
| JM-2921 | $K_7[A-a-GeNb_3W_9O_{40}].18H_2O$ | |
| JM-2922 | $K_7[A-b-SiNb_3W_9O_{40}].20H_2O$ | |
| JM-2923 | $(Me_3NH)_9[A-a-HSi_2Nb_6W_{18}O_{78}]$ | |
| JM-2924 | $(Me_3NH)_9[A-a-HGe_2Nb_6W_{18}O_{78}]$ | |
| JM-2925 | $(Me_3NH)_9[A-a-HGe_2Nb_6W_{18}O_{78}]$ | |
| JM-2926 | $K_7(H)[A-a-Ge_2Nb_6W_{18}O_{77}].18H_2O$ | |
| JM-2927 | $K_8[A-b-Si_2Nb_6W_{18}O_{77}]$ | |
| JM-2928 | $(Me_3NH)_8[A-b-Si_2Nb_6W_{18}O_{77}]$ | |

[a]NMP = N-methylpyrrolidinone.
[b]DMA = N,N-Dimethylacetamide.
[c]HISH[30] = Histidinium
[d]LYSH[+] = Lysinium
[e]ARGH[+] = Argininium
[f]TBA = Tetrabutylammonium Preferred polyoxometalates to be used in the present invention include HS-042, HS-053, HS-057, HS-058, HS-105, HS-106, HS-131, and HS-158. Particularly preferred are HS-058.

The present invention may be carried out by administering the polyoxomethalate directly to the lungs of the animal being treated. Preferably, the polyoxometalate is administered in the form of an aerosol.

The viral infections which may be treated by the present method include influenza A, influenza B, and RSV. Preferably, the present method is used to treat influenza A or RSV.

The present method may be used to treat respiratory viral infections in mammals such as humans, cats, horses, cows, pigs, sheep, monkeys, rabbits, rats, mice, etc., and birds such a chickens and turkeys.

Although the exact dosage of polyoxometalate to be administered will depend on the exact type, size, and condition of the animal being treated, the exact viral infection being treated, and the identity of the polyoxometalate being administered, good results are typically achieved with dosages of 0.1 to 100 mg/kg of body weight, preferably 1 to 30 mg/kg of body weight.

In certain circumstances, it may be preferred to coadminister the polyoxometalate with an additional active agent such as amantadine, rimantadine, or ribavivin. Of course, the present method may be carried out by administering a single polyoxometalate or a combination of two or more polyoxometalates.

In a preferred embodiment, the present invention provides a method for preventing respiratory viral infections. In this embodiment, the polyoxometalate is administered to a subject which has not been diagnosed as suffering from a respiratory viral infection but is considered to belong to an at risk population. With the exception of the subject to whom the polyoxometalate is administered this preventative embodiment is carried out as described above for the present method of treatment.

Examples of subjects in an at risk population to be administered polyoxometalate in the present method of prevention include subjects not yet suffering from a respiratory viral infection but in close contact with another individual, already diagnosed as suffering from a respiratory viral infection, such as a neonate or infant in a nursery in which at least one other neonate or infant has been diagnosed as suffering from a respiratory viral infection or a member of a barrack, nursing home, or school in which at least one other member has been diagnosed as suffering from a respiratory viral infection. Another at risk population is the elderly in general during flu season.

In another embodiment, the present invention provides pharmaceutical compositions which comprise a polyoxometalate for the treatment of a respiratory viral infection. Suitably, the compositions of the present invention are in a form which is conveniently administered as an aerosol spray.

The term aerosol includes compositions of matter in which particles or droplets are suspended or dispersed in a gaseous medium such a air. Thus, the term aerosol includes sprays. Apparatus and methods for forming aerosols are disclosed in Kirk-Othmer, *Encyclopedia of Chemical Technology*, 4th Ed., vol. 1, Wiley, New York, pp. 670–685 (1991) and Kirk-Othmer, *Encyclopedia of Chemical Technology*, 3rd. Ed., vol. 21, Wiley, New York, pp. 466–483 (1983), both of which are incorporated herein by reference.

The administration of the aerosol spray containing the polyoxometalate may be conveniently carried out by means of a delivery system capable of delivering an aerosol spray. Such delivery systems include conventional nasal aerosol spray bottles, or aerosol delivery via commonly used respiratory mechanical ventilation support equipment.

Typically, the present compositions will be in the form of an aqueous solution or dispersion of the polyoxometalate. The concentration of the polyoxometalate is suitably 0.1 µg/ml to 10 mg/ml, preferably 10 µg/ml to 1 mg/ml. The composition may further comprise a pH adjusting agent such as a physiologically tolerated acid or base, a buffer, or another active agent, such as ribavirin amantadine or rimantadine.

The present invention also provides dispensing devices for administering the present pharmaceutical compositions. Such dispensing devices comprise a container means which contains a pharmaceutical composition comprising the polyoxometalate and optionally another active ingredient; and means for forming an aerosol of the pharmaceutical composition. Suitable container means and suitable means for forming an aerosol are described in Kirk-Othmer, *Encyclopedia of Chemical Technology*, 4th Ed., vol. 1, Wiley, New York, pp. 670–685 (1991) and Kirk-Othmer, *Encyclopedia of Chemical Technology*, 3rd. Ed., vol. 21, Wiley, New York, pp. 466–483 (1983), both of which are incorporated herein by reference. Suitable container means include metal cans and glass and plastic bottles. Suitable means for forming an aerosol include combinations of propellants and valves (including an actuator and dip tube). A propellant may be present in the container under pressure, or the material in the container may be propelled by pressure created by mechanical force means such as, e.g., a bellows, bulb, or pump. Preferably, the present dispensing means is a pressurized aerosol can or an atomizer.

The present invention will no be described in more detail by referring to specific embodiments, which are not intended to be limiting.

Polyoxometalates have a broad spectrum of antimyxovirus activity. Several sulfates polysaccharides which have anionic charge inhibited adsorption of HIV, HSV, FluV-A and RSV, whereas they did not inhibit the adsorption of FluV-B, MLSV, SSPE, virus and PFluV-3 (Hosoya, M., et al, *Antimicrob. Agents Chemother.*, vol. 35, pp. 2515–2520 (1991)). On the other hand, some polyoxometalates examined in this study had antiviral effects against FluV-A, RSV, MLSV, FluV-B, and PFluV-2. Inasmuch as the causative agents of viral respiratory infections are not rapidly identifiable by clinical diagnosis and there is a need for early treatment of patients to prevent the progress of infection, it is necessary to use a broad spectrum antiviral drug for the treatment of acute respiratory viral infections. From this point of view, HS-058 which shows a potent antiviral activity against FluV-A, FluV-B, RSV, MLSV, and PFluV-2 is especially preferred, because these viruses are the main causative agents of acute viral respiratory diseases (Hilleman, M. R., et al, *J. Amer. Med. Assoc.*, vol. 180, pp. 444–453 (1962).

The structure-activity relationship of polyoxometalates and antimyxoviral activity was insightful. From our examination of 25 polyoxometalates against myxoviruses, 4 compounds emerged which showed potent and broad spectrum of antiviral activity. Among them, 2 compounds HS-054 and HS-058 are so-called "sandwich structures", HS-106 is a "double Keggin structure" and HS-158 is a hexasubstituted Wells-Dawson structure. HS-054 was apparently more potent in antiviral activity and less cytotoxic than its precursor complex (HS-042). The precursor complex of HS-058 and HS-106, HS-015 ($PW_9O_{34}^{9-}$), was not examined in this study for antimyxoviral activities but it was shown to be less effective against HIV-1 in a previous report (Hill, C. L., et al, *J. Med. Chem*, vol. 33, pp. 2767–2772 (1990)). The most effective compounds had Nb or Fe-base units ($MO_6$ octahedra, M=Nb or Fe) joining two halves of the molecule.

HS-058, one of the most active polyoxometalates did not inhibit the adsorption of FluV to MDCK cells and agglutination of chick erythrocytes by FluV-A, whereas it did inhibit hemolysis of chick erythrocytes after adsorption of virus at 4° C. as shown in Table 4, HS-058 did not inhibit FluV infection in MDCK cells when it was added at the time of virus adsorption (1 hour before to 1.5 hours after virus inoculation), whereas it did inhibit infection when it was present after virus adsorption for the whole course of the experiment (1 hour before to 120 hours after virus inoculation; FIG. 1 and Table 4). HS-058 was also inhibitory against FluV-A infection when it was added after virus adsorption to the end of culture (1.5 to 120 hours in Table 4). It is likely that polyoxometalates do not inhibit FluV adsorption to cellular membrane, but inhibit the fusion of the cleaved HA molecule and the cellular membrane. A similar result was reported using sulfated polysaccharides by Hosoya et al. (Hosoya, M., et al, *Antimicrob. Agents Chemother.*, vol. 35, pp. 2515–2520 (1991)).

An insight on the mechanism of antiviral activity of HS-058 against FluV-A is apparent from the experiments on inhibition of virus replication in MDCK cells. When cells were infected with virus at a high moi and then treated with 4 $EC_{50}$ of HS-058, HS-058 had no effect on the yield of infectious Flu-V relative to control. However, when cells were infected with low moi of virus and then treated with HS-058, it inhibited virus yield relative to control. Clearly, HS-058 did not inhibit the growth of infectious virus in single cells, but inhibited the spread of virus from infected to uninfected cells.

HS-058 did not inhibit the antigen synthesis and plaque formation of RSV when it was added after the virus adsorption (Tables 4 and 5, FIG. 2). In contrast to the result with FluV, HS-058 inhibited strongly RSV infection in HeLa cells when it was added during the time of virus adsorption. HS-058 inhibited syncytium formation of HeLa cells by RSV infection. It appears that the antiviral mechanism of the polyoxometalate HS-058 occurs at two important points during virus-cell interactions. The first is adsorption of RSV to cell membrane and penetration (hemolysis) of FluV-A into cells. The second point is the late stage of virus infection by inhibiting cell-to-cell spread of RSV and FluV-A.

Of not was the recognition that several of the polyoxometalates which exhibited selective anti-HIV-1 activity were also potent antiviral agents against FluV-A (Table 2). This parity was not as strong with RSV or MLSV. HS-058 is a compound with modest anti-HIV-1 activity comparable to 2',3'-dideoxyinosine, a compound approved for the treatment of HIV.

The present invention also provides a method for treating human herpesvirus infection by administering a polyoxometalate. In the context of the present invention, the term human herpesvirus infection includes not only herpes simplex virus type 1 but also herpes simplex virus type 2 and cytomegalovirus. The present method specifically includes the treatment of herpes simplex virus type 1 (HSV-1), herpes simplex virus type 2 (HSV-2), cytomegalovirus (CMV), Epstein-Barr virus (EPV), human herpesvirus type 6 (HHV-6), human herpesvirus type 7 (HHV-7), and human herpesvirus type 8 (HHV-8). The preferred mode of administration for HSV-1, and HSV-2 is topical administration in the form of a cream containing 0.1 to 5% by weight, based on the total weight of the cream, of the polyoxometalate. In addition, the polyoxometalate may be administered systemically. For the other human herpesvirus infections, systemic administration is preferred, more preferably intravenous administration. The dosage range for the treatment of herpesvirus infection is the same as that used for the treatment of respiratory viral infection discussed above.

In another embodiment, the present invention provides a method for treating hepadnavirus infection, in particular hepatitis B virus (HBV), by administering a polyoxometalate. In this case, systemic administration is preferred, more preferably intravenous administration. Again, the dosage ranges for the treatment of hepadnavirus infection are the same as discussed above for the respiratory viral infection treatment.

In the case of treating herpes virus infection, and hepadnavirus infection, it is not only possible to use the polyoxometalate compounds discussed above, but in addition, it is possible to use the polyoxometalate compounds discussed in Ikeda et al, *Antiviral Chemistry & Chemotherapy*, vol. 4, pp. 253–262 (1993), which is incorporated herein by reference in its entirety.

Other features of the invention will become apparent in the course of the following descriptions of exemplary embodiments which are given for illustration of the invention and are not intended to be limiting thereof.

EXAMPLES

Materials and Methods

Chemicals. Twenty five compounds were submitted to the antiviral assay (see Table 1 above) and synthesized according to the procedures which are published elsewhere. (Droege, M. W., et al, *J. Mol. Catal.*, vol. 69, p. 323 (1991); Finke, R. G., et al, *J. Am Chem. Soc.*, vol. 106, pp. 7274–7277 (1984); Finke, R. G., et al, *Inorg. Chem.*, vol. 26, pp. 3886–3896 (1987); Hill, C. L., et al, *J. Med. Chem.*, vol. 33, pp. 2767–2772 (1990); Hill, C. L., et al, in *Advances in Chemotherapy of AIDS*, Diasio, R. B. et al, Eds., Pergamon Press, New York, pp. 33–41 (1990); Kim, G.-S., et al, *J. Med. Chem.*, vol. 37, pp. 816–820 (1994); Kim, G.-S., et al, unpublished work; Lyon, D. K., et al, *J. Am. Chem. Soc.*, vol. 113, pp. 7209–7221 (1991), Weeks, M. S., et al, *J. Med. Chem.*, vol. 35, pp. 1216–1221 (1992)). Dextran sulfates were purchased from Sigma Chemical Co. (St. Louis, Mo.).

Virus and cells. FluV, A/Ishikawa/7/82 (H3N2) and B/Sinagapore/222/79 had been passed more than 20 times in embryonated eggs. Both viruses were passed twice in Madin-Darby canine kidney (MDCK) cells before being used for virus growth or growth inhibition experiments in MDCK cells. RSV Long strain (type-A) had been passed in HEp-2 cells more than 20 times. Fresh isolates of RSV FM-58-8 (type-A) and SM-61-48 (type-B) were passed 5 times in HEp-2 cells after isolation. Measles virus (MLSV) Edmonston strain, mumps virus (MPSV) ECXH-3 strain, parainfluenzavirus (PFluV) type 2, Greer strain and (PFluV) type 3, C243 strain were passed 10 times in Vero cells, and MLSV, MPSV, and PFluV-2 were passed an additional 3 times in HMV-2 cells (Nishimura, H. K., et al, *J. Gen. Virol.*, vol. 70, pp. 1653–1661 (1989)). Sources of virus strains and culture cell lines used for studies with the myxoviruses have been reported previously (Shigeta, S., et al, *Antiviral Chem. Chemother.*, vol. 3, pp. 171–177 (1992); Shigeta, S., et al, *Antimicrob. Agents Chemother.*, vol. 36, pp. 435–439 (1992).

MDCK, HEp-2, HMV-2 and Vero cells were cultured in Eagle's minimal essential medium (MEM) supplemented with 10% newborn calf serum, 100 units of penicillin G, and 100 mg of streptomycin per ml. For the infections of HEp-2 cells with RSV, HMV-2 cells with any of MLSV, MPSV and PFluV-2 and Vero cells with PFluV-3, a maintenance medium consisting of MEM with 2% heat=inactivated fetal calf serum and antibiotics was used. For the infection of MDCK cells with FluV, a maintenance medium consisting of MEM containing 0.2% bovine albumin, 2.5 µg/ml of crystallized trypsin (Sigma Chemical Co., St. Louis, Mo.) and antibiotics was used. For the plaque assay of RSV, HeLa cells grown in MEM supplemented with 10% newborn calf serum, 1.6% glucose and antibiotics, and MM consisting of MEM with 2% fetal calf serum, 1.6% glucose, antibiotics and 0.7% methyl cellulose (Methocel A-4M Premium; Dow Chemical Co. Midland Mich.) were used.

Antiviral assay. Antimyxovirus evaluation was principally followed the MTT assay by Pauwels et al. (Pauwels, R., et al, *J. Virol. Meth.*, vol. 20, pp. 309–321 (1988). Four-fold dilution of compound (100 µl) was prepared in a 96 well tissue culture tray (Nunclon, 96 wells, Nunc A/S, Roskilde, Denmark) with 4 wells each for one dilution and combined with $10^4$ cells (50 µl) and 100 $TCID_{50}$ of virus (50 µl). The tray was centrifuged at 700 g for 5 minutes and incubated at 35° C. for 4 to 5 days. During the incubation, the culture medium with or without compound was changed after 3 days. To determine the median effective antiviral concentration ($EC_{50}$), we added 20 ml of 3-(4,5-dimethylthiazol-2-yl)-2,5-diphenyltetrazolium bromide (MTT) at a concentration of 7 µg/ml in phosphate buffered saline (PBS, pH 7.2) to each well of cultures. The mixture was incubated at 37° C. for 2 hours and reduced MTT (formazan) was extracted by adding 100 µl of acidic isopropanol containing 4% Triton-X. The absorbance of blue color of formazan was measured using a computer controlled microplate reader (Model 3550, Bio Rad, Hercules, Calif.) at two different wavelengths (540 and 690 nm). The $EC_{50}$ was expressed as the concentration that achieved the 50% protection of virus infected cells from the virus induced destruction. The percent protection was calculated by the following formula:

$$[(OD_T)V-(OD_C)V]/[(OD_C)M-(OD_C)V]\times 100(\%),$$

where $(OD_T)V$, $(OD_C)V$ and $(OD_C)M$ indicate the absorbance of the test sample, the virus infected control (no compound), and the mock infected control (no virus and no compound), respectively.

Antiviral activity against RSV was examined by a plaque reduction method. Monolayer cultures of HeLa cells were treated with 4-fold dilution of compound and infected with 50 plaque forming units (PFU) of virus. Virus and compound were diluted in maintenance media containing 0.7% methylcellulose. Infected cultures were incubated at 35° C. for 4 days, fixed with 5% formalin in PBS, stained with 0.02% crystal violet and the number of plaque in monolayer was counted under a microscope (40× magnification). The concentration of compound which reduced the number of plaques to 50% of the control was determined as the $EC_{50}$.

The anti-HIV-1 activity of the compounds was determined in human PBM cells as described previously (Schinazi, R. F., et al, *Antimicrob. Agents Chemother.*, vol. 36, pp. 2423–2431 (1992)). Sterile stock solutions (40 mM) of the new compounds were prepared in water and then diluted to the desired concentration in medium. Cells were infected with the prototype HIV-$1_{LA1}$ at a multiplicity of infection of 0.01. Virus obtained from the cell supernatant was quantitated on day 6 after infection by a reverse transcriptase assay using poly$(rA)_n$·oligo$(dT)_{12-18}$ as template-primer. Studies have indicated a strong correlation ($r^2 \geq 0.88$) between results obtained using the reverse transcriptase assay and a commercial HIV-1 p24 assay for polyoxometalates. The toxicity of the compounds was assessed in human PBM cells, as described previously (Schinazi, R. F., et al, *Antimicrob. Agents Chemother.*, vol. 36, pp. 2423–2431 (1992)). The $EC_{50}$ and median inhibitory concentration ($IC_{50}$) were obtained from the concentration-response curve using the median effective method described by Chou and Talalay (Chou, T.-C., et al, *Adv. Enzyme Regul.*, vol. 22, pp. 27–55 (1984)).

Immunofluorescent staining of RS virus infected cells. HeLa cells were seeded in Lab-Tek chamber slide (8 chambers, Nunc Inc.. Naperville, Ill.) and incubated at 37° C. in 5% $CO_2$. When the cell monolayer became confluent, approximately 50 PFU of RSV was inoculated in each well of the chamber. The cultures were incubated at 35° C. in a 5% $CO_2$ incubator. At 48 hours after infection, the maintenance media was removed, the cells were washed with PBS (pH, 7.2), and fixed with acetone for 10 minutes at room temperature. The fixed cells were stained with fluorescein isothiocyanate conjugated rabbit antibodies against RSV (Denka Seiken Co., Niigata, Japan) for 30 minutes at 37° C., mounted with 20% glycerol in PBS, and analyzed for immunofluorescence under a fluorescent microscope (Nikon Optiphot+EFD2, Nikon Industrial Co., Tokyo, Japan). Inhibitory effects of the compounds on RSV antigen synthesis and syncytium formation were monitored by counting the number of antigen positive foci or cells in a syncytium after immunofluorescent staining of infected cells. The details for the immunofluorescence for RSV were reported elsewhere (Shigeta, S., et al, *Antiviral Chem. Chemother.*, vol. 3, pp. 171–177 (1992)).

Hemagglutination, hemolysis by influenzavirus, and inhibition assay. Fresh FluV-A was obtained from allantoic fluid of infected embryonated chicken egg. The virus was 2-fold diluted with PBS (pH 7.2), 100 μl distributed each to wells of a microtray, combined with the same volume of 0.5% fresh chicken erythrocytes, and was left at 4° C. for 1 hour. Titer of hemagglutinin (HA) of the virus was determined as 256 units/100 μl. After the hemagglutination, erythrocytes were centrifuged at 700 g for 5 minutes, resuspended in fresh 0.1 M sodium acetate buffer solution (pH, 5.25), and incubated at 37° C. for 30 minutes. The procedure reported by Huang et al (Huang, R. T. C., et al., *Virology*, vol. 110, pp. 243–247 (1981)) for hemolysis studies by FluV-A was followed. Maximum hemolysis was determined by absorbency at 540 nm which measures hemoglobin. For the inhibition of hemagglutination by the compounds, 2-fold dilutions of compound in PBS (pH 7.2) (100 μl), and 4 HA units of FluV-A (100 μl) were combined with 0.5% chick erythrocytes (200 μl), and the mixture was left at 4° C. for 1 hour. The minimal concentration of compounds which inhibited hemagglutination was determined as the minimal inhibitory dose (MID). For the inhibition of hemolysis, chick erythrocytes were agglutinated in several wells of a microtray by 100 units of HA following the procedure above. After hemagglutination, buffer was replaced with 2-fold dilution of compound in acetate buffer solution (pH 5.25), and the mixture was incubated at 37° C. for 30 minutes. The minimal concentration of compound which reduced the absorbance at 540 nm by 50% of control was defined as the $EC_{50}$.

RESULTS

Antiviral activities of several polyoxometalates against ortho- and paramyxoviruses. Twenty-five compounds (see Table 1 above) were evaluated for their inhibitory activities on the cytopathic effect of FluV-A, RSV and MLSV in tissue culture cells by MTT method. Among the compounds examined, 24 demonstrated antiviral activity against FluV-A, 11 showed activity against RSV, and 6 were effective against MLSV at lower concentrations than the cytotoxicity to each host cell (see Tables 2 and 3). Among the effective compounds. HS-054 or $[Na_{16}Fe_4(H_2O)_2(P_2W_{15}O_{56})_2 \cdot nH_2O]$ (Wells-Dawson sandwich structure), HS-058 or $[K_{10}Fe_4(H_2O)_2(PW_9O_{34})_2 \cdot nH_2O]$ (Keggin sandwich structure), HS-106 or $[(Me_3NH)_8Si_2W_{18}Nb_6O_{77} \cdot nH_2O]$ (double Keggin structure), and HS-158 or $(K_{12}Nb_6P_2W_{12}O_{62})$ (hexasubstituted Wells-Dawson structure) exhibited potent and broad-spectrum antimyxovirus activities. These 4 compounds were further examined for antiviral activities against 9 myxovirus strains including an additional 6:FluV-B, MPSV, PFluV-2, PFluV-3, RSV-A, and RSV-B. Two RSV strains were fresh isolates from patients. The results shown in Table 3 indicate that FluV-A, FluV-B, RSV, MLSV, and PFluV-2 were susceptible to all 4 compounds at concentrations from 0.3 to 45.7 μM. On the other hand, MPSV and PFluV-3 were susceptible only to HS-054 at relatively high concentrations (21 to 28 μM). HS-058 showed $EC_{50}$ values of 1.4 μM against FluV-A, 13.9 μM against FluV-B, 5.6 μM against RSV (Long strain), 0.8 μM against MLSV and 0.43 μM against PFlu-V-2. HS-058 was not inhibitory for MPSV and PFluV-3 at 50 μM. HS-058 and HS-106 were less cytotoxic to MDCK and HEp-2 cells than HS-054 and HS-158, but more toxic to HMV-2 cells than the latter cell lines. HS-058 was not cytotoxic up to 200 μM for MDCK and HEp-2 cells, but had an $IC_{50}$ value of 50 μM for HMV-2 and Vero cells.

TABLE 2

ANTIVIRAL ACTIVITY OF POLYOXOMETALATES
FOR MYXOVIRUSES AND HIV-1 IN VITRO

| | Antiviral activity, $EC_{50}$ μM | | | | Cytotoxicity, $IC_{50}$ μM | | | |
|---|---|---|---|---|---|---|---|---|
| Compound | FluV-A | RSV | MLSV | HIV-1 | MDCK | HEp-2 | HMV-2 | PBM |
| HS-005 | <u>1.8</u>[a] | 1.9 | 1.5 | <u>0.4</u> | 50 | 1.9 | 26.0 | 35.0 |
| HS-008 | <u>6.3</u> | >50 | >43 | <u>0.3</u> | >100 | 50.0 | 43.0 | >100 |
| HS-010 | <u>1.2</u> | <u>0.9</u> | <u>1.9</u> | 0.9 | >100 | 12.4 | 30.0 | 1.8 |
| HS-026 | <u>0.23</u> | >1.1 | >3.7 | <u>0.3</u> | 16.0 | 1.1 | 3.9 | 7.7 |
| HS-042 | <u>2.7</u> | >8.6 | >16.2 | <u>4.7</u> | >100 | 8.6 | 20.4 | >100 |
| HS-052 | <u>0.9</u> | >2.7 | >0.8 | <u>0.1</u> | >100 | 2.7 | 1.0 | 39.2 |
| HS-053 | <u>1.1</u> | <u>1.4</u> | >28.1 | <u>0.3</u> | 100 | >50 | 25.6 | 4.5 |
| HS-054 | <u>0.7</u> | <u>1.4</u> | <u>0.2</u> | <u>0.4</u> | >100 | >50 | >50 | 20.8 |
| HS-055 | <u>2.0</u> | >26 | >16 | <u>1.6</u> | 100 | 26.0 | 22.0 | 91.5 |
| HS-056 | 21.1 | >22 | >1.6 | <u>4.5</u> | 50 | 22.0 | 1.8 | 93.1 |

TABLE 2-continued

ANTIVIRAL ACTIVITY OF POLYOXOMETALATES FOR MYXOVIRUSES AND HIV-1 IN VITRO

| Compound | Antiviral activity, $EC_{50}$ $\mu M$ | | | | Cytotoxicity, $IC_{50}$ $\mu M$ | | | |
|---|---|---|---|---|---|---|---|---|
| | FluV-A | RSV | MLSV | HIV-1 | MDCK | HEp-2 | HMV-2 | PBM |
| HS-057 | <u>1.1</u> | >50 | 20.6 | <u>1.3</u> | 100 | >50 | 31.0 | >100 |
| HS-058 | <u>1.1</u> | 3.8 | <u>0.76</u> | <u>1.7</u> | >100 | >50 | 50.0 | >100 |
| HS-083 | >35 | >9.3 | 23.6 | <u>36.2</u> | 35.2 | 9.3 | 31.0 | >100[b] |
| HS-089 | 11.2 | >3.7 | >50 | 51.5 | 71.7 | 37.0 | 50.0 | >100[b] |
| HS-091 | <u>3.8</u> | 1.6 | >80 | <u>0.2</u> | 50.0 | 6.2 | 8.0 | 5.9[b] |
| HS-105 | <u>5.0</u> | 4.5 | >50 | <u>0.6</u> | 100 | >50 | >50 | >100[b] |
| HS-106 | <u>3.6</u> | >9.3 | >50 | <u>0.3</u> | 100 | 9.3 | >50 | >100[b] |
| HS-131 | <u>2.5</u> | 9.2 | >50 | <u>0.8</u> | 85.6 | 47.1 | 50.0 | >100[b] |
| HS-132 | <u>13.4</u> | 7.8 | >50 | <u>0.8</u> | >100 | 50.0 | 50.0 | >100[b] |
| HS-133 | <u>4.0</u> | 5.1 | >10 | <u>1.4</u> | 100 | >50 | 27.0 | >100[b] |
| HS-136 | <u>10.0</u> | >50 | >50 | <u>2.0</u> | 100 | >50 | >50 | >100[b] |
| HS-144 | <u>11.4</u> | <u>7.3</u> | 29 | <u>0.2</u> | >100 | >50 | 37.6 | >100[b] |
| HS-146 | <u>2.2</u> | 1.0 | >4.5 | <u>0.2</u> | 56.6 | 8.0 | 12.8 | 49.7[b] |
| HS-157 | <u>2.1</u> | 11.6 | >50 | <u>0.1</u> | 100 | 11.6 | >50 | 58.4[b] |
| HS-158 | <u>1.5</u> | >10 | <u>1.2</u> | <u>0.3</u> | >100 | 10.0 | 44.2 | 75.0[b] |
| Ribavirin | 8.7 | 4.7 | 5.2 | NA | >100 | >50 | >100 | NA |

[a]Underline indicates that the effective antiviral concentration is at least 10-fold below the cytotoxic concentration. The variance for duplicate or triplicate assays was less than 15%.
[b]Cytotoxicity determined by $^3$H-thymidine uptake instead of cell proliferation.

TABLE 3

INHIBITORY EFFECTS OF 4 POLYOXOMETALATES AGAINST SEVERAL ORTHO- AND PARAMYXOVIRUSES

| Virus strain | $EC_{50}$[a] and $IC_{50}$ of Polyoxometalates, AM | | | | |
|---|---|---|---|---|---|
| | HS-054 | HS-058 | HS-106 | HS-158 | Ribavirin |
| Antiviral Activity | | | | | |
| FluV-A | 0.59 | 1.4 | 2.8 | 2.8 | 3.7 |
| (Ishikawa) | (0.37–0.94) | (0.7–2.0) | (1.3–5.4) | (1.0–5.5) | (1.8–7.0) |
| FluV-B | 35.5 | 13.9 | 45.7 | 36.5 | 5.1 |
| (Singapore) | (20–54) | (8.7–21.8) | (19.4–68) | (30–43) | (1.8–5.2) |
| RSV-A | 2.8 | 5.6 | 9.8 | 14.2 | 4.7 |
| (Long) | (9.4–4.5) | (2.4–13.5) | (9.0–10.3) | (8.3–24.4) | (1.5–9.7) |
| RSV-A | 5.0[b] | 23.0 | 10.0 | 8.5 | 3.5 |
| (FM-58-8) | | | | | |
| RSV-B | 7.6[b] | 3.1 | 4.5 | 2.7 | 1.6 |
| (SM61-48) | | | | | |
| MLSV | 0.3 | 0.8 | 6.6 | 1.4 | 5.2 |
| (Edmonston) | (0.2–0.4) | (0.76–0.85) | (5.6–7.6) | (1.23–1.61) | (1.9–10.0) |
| MPSV | 20.6 | >50 | >50 | >50 | 3.4 |
| (EXCH-3) | (15.5–20) | (3.1–37.1) | | | |
| PFluV-2 | 1.8 | 0.43 | 7.8 | 24.1 | 8.9 |
| (Greer) | (1.5–2.1) | (0.32–0.54) | (2.6–16.1) | (23.2–25.0) | (6.4–11.2) |
| PFluV-3 | 28.0 | >50 | >50 | >50 | 17.2 |
| (C243) | (25–31) | | | | (16.4–18.0) |
| Cytotoxicity[c] | | | | | |
| MDCK | >200 | >200 | >200 | 164 | >200 |
| | (>200)[c] | (>200) | (200) | (166) | (>200) |
| HEp-2 | 88 | >200 | >200 | 82.7 | 52.7 |
| | (38.0) | (80.5) | (192.2) | (69.4) | (>200) |
| HMV-2 | >200 | 50 | 20.7 | 53.7 | >100 |
| | (94.1) | (52.2) | (70.7) | (73.1) | (>100) |
| Vero | 50 | 50 | 148 | >200 | 100 |
| | (37.5) | (38.4) | (>200) | (41.4) | (>200) |

[a]Average of 3 to 4 independent experiments. Numbers in parentheses show the range of values.
[b]Data from one experiment.
[c]$IC_{50}$ was examined by MTT method and viable cell counting. The data in parentheses indicate the results of viable cell counting.

Antiviral Effect of HS-058 Added Before, During, and After Virus Adsorption

In order to analyze the mechanism of antiviral activity of HS-058 against FluV-A and RSV, the compound was added to host cells before, during, and after virus infection. For the antiviral assay against FluV-A, MDCK cells were used and examined by MTT assay. For the assay against RSV, HeLa cells monolayers were used and examined by a plaque reduction method. As shown in Table 4, when HS-058 was added to the culture at 1 hour before the virus inoculation and maintained throughout the experiment, it was inhibitory against FluV-A at less than 0.7 $\mu$M and against RSV at 2.0 $\mu$M. When HS-058 was added to the culture 1 hour before and removed from the culture 1.5 hours after the virus inoculation, it was inhibitory against RSV at 2.4 $\mu$M, but was not inhibitory against FluV-A. When the compound was added after the virus adsorption (at 1.5 hour) and removed 3 hours after infection it was not inhibitory against both FluV-A and RSV. On the other hand, when the compound was added after virus adsorption and maintained throughout the experiment, it was inhibitory against both viruses at 4.1 and 5.8 $\mu$M (Table 4).

TABLE 4

TIME OF ADDITION AND INHIBITORY EFFECTS OF HS-058 ON INFLUENZA AND RESPIRATORY SYNCYTIAL VIRUS REPLICATIONS

| Time of addition of compound (hours)[a] | $EC_{50}(\mu M)$ against: | |
|---|---|---|
| | FluV-A(Ishikawa) | RSV(Long) |
| −1 to 120 | 0.7 | 2.0 |
| −1 to 1.5 | >20 | 2.4 |
| 1.5 to 120 | 4.1 | 5.8 |
| 1.5 to 3 | >31 | >20 |

[a]Time of addition before or after virus inoculation. Cells were washed extensively after removal of compound.

Inhibitory Effect of HS-054 and HS-058 Against Hemagglutination and Hemolysis of Chick Erythrocytes by Influenzavirus Type A FluV-A binds to chick erythrocytes membrane at 4° C. in neutral buffered solution and hemolysis occurs at 37° C. in weakly acidic solution. The inhibitory effect of HS-054 and HS-058 against hemagglutination by 4 units of viral-HA and hemolysis by 100 units of viral-HA was examined. As shown in Table 5, both compounds did not inhibit hemagglutination at 100 $\mu$M, but inhibited hemolysis at 80 and 58 $\mu$M, respectively. On the other hand, dextran sulfates did not inhibit hemagglutation and hemolysis at all.

TABLE 5

INHIBITORY EFFECTS OF HS-058 FOR HEMAGGLUTINATION, HEMOLYSIS OF INFLUENZA VIRUS AND ANTIGEN SYNTHESIS, SYNCYTIUM FORMATION OF RESPIRATORY SYNCYTIAL VIRUS

| Compound | Anti-FluV-A activity ($\mu$M) Inhibition for: | | Anti-RSV activity ($\mu$M) Inhibition for: | |
|---|---|---|---|---|
| | HA | Hemolysis | Antigen | Syncytium |
| HS-054 | >200 | 80(56–88)[a] | >200 | 3.6(2.5–4.2) |
| HS-058 | >200 | 58(350–81)[a] | >200 | 8.5(6.5–13) |
| DS-8000[b] | >200 | >200[c] | >200[c] | >200[c] |
| DS-50000[b] | >200 | >200 | >200[c] | >200[c] |

[a]Average of 2 to 3 independent experiments. Numbers in parentheses show range of value.
[b]Molecular weights of dextran sulfates.
[c]Concentrations are expressed as $\mu$g/ml.

Inhibitory Effect of HS-054 and HS-058 Against Syncytium Formation by Respiratory Syncytial Virus The inhibitory effect of HS-054 and HS-058 against syncytium formation of RSV in HeLa cell monolayers was examined by immunofluorescence. Both compounds inhibited syncytium formation of HeLa cells by RSV at 3.6 and 8.5 $\mu$M, respectively, but did not inhibit viral specific antigen synthesis at 100 $\mu$M (Table 5 and FIG. 2). Dextran sulfates did not inhibit antigen synthesis and syncytium formation at 100 $\mu$M.

Inhibitory Effect of HS-058 on One Step Growth of FluV-A in MDCK Cells

A 2-day culture of MDCK cells with confluent monolayer cells was prepared in 50 ml Nunclon tissue culture plates. Two sets of virus infected cultures were prepared. One set was infected with a high moi (5.0) and the other with a low moi (0.005). Both sets included virus control cultures which did not contain HS-058 throughout the experiment. Experimental cultures were treated with 4.4×$EC_{50}$ of the compound (6.0 $\mu$M) before (60 min) and after (90 min) virus inoculation while maintaining the compound throughout the culture period. Four to five flasks, prepared for each control and experimental cultures, were sampled at the time indicated in FIG. 1. The flasks were frozen at −80° C., thawed at 37° C., centrifuged at 700 g for 10 min and then titrated for yield of infectious virus in the supernatant. As shown in FIG. 1a, in the culture infected with high moi, HS-058 inhibited virus replication when added to cultures before virus adsorption, but was not inhibitory when added after virus adsorption to cells. In contrast, HS-058 inhibited virus yield production when the culture was infected with virus at a low moi, even when the compound was added after virus adsorption. These results indicate that the compound inhibits the virus adsorption and also cell-to-cell spread of virus.

Anti-HIV-1 Activity in Human Lymphocytes

Of the 25 compounds evaluated in acutely infected primary human PBM cells, 23 compounds demonstrated activity below 5 $\mu$M (Table 2). HS-008, HS-106, and HS-144 had a selectivity index greater than 300 and had no cytotoxicity to uninfected PBM cells when evaluated up to 100 $\mu$M. HS-058 was a modest inhibitor of HIV-1 with an $EC_{50}$ of 1.7 $\mu$M and no apparent cytotoxicity in any of the 4 different cells used.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for preventing respiratory viral infection, comprising administering to a subject at risk an effective amount of a polyoxometalate selected from the group consisting of $[(NMP)_2H]_3PW_{12}O_{40}$
$[(DMA)_2H]_3PMo_{12}O_{40}$
$(NH_4)_{17}Na[NaSb_9W_{21}O_{86}]$
a- and b-$H_5BW_{12}O_{40}$
a- and b-$H_6ZnW_{12}O_{40}$
a- and b-$H_6P_2W_{18}O_{62}$
$\alpha$-$(NH_4)_6P_2W_{18}O_{62}$
$K_{10}Cu_4(H_2O)_2(PW_9O_{34})_2 \cdot 20H_2O$
$K_{10}Co_4(H_2O)_2(PW_9O_{34})_2 \cdot 20H_2O$
$Na_7PW_{11}O_{39}$
$Na_7PW_{11}O_{39} \cdot 20H_2O + 2C_6H_5P(O)(OH)_2$
$(n\text{-}Bu_4N)_4H_3PW_{11}O_{39}$
b-$Na_8HPW_9O_{34}$
$(n\text{-}Bu_4N)_3PMoW_{11}O_{39}$
a-$[(nBu)_4N]_4Mo_8O_{26}$
$(n\text{-}Bu_4N)_2W_6O_{19}$
$(n\text{-}Bu_4N)_2Mo_6O_{19}$
a-$(NH_4)_nH_{(4-n)}SiW_{12}O_{40}$
a-$(NH_4)_nH_{(5-n)}BW_{12}O_{40}$
a-$K_5BW_{12}O_{40}$
$K_4W_4O_{10}(O_2)6$
b-$Na_9HSiW_9O_{34}$
$Na_6H_2W_{12}O_{40}$
$(NH_4)_{14}[NaP_5W_{30}O_{110}]$
a-$(NH_4)_5BW_{12}O_{40}$
a-$Na_5BW_{12}O_{40}$
$(NH_4)_4W_{10}O_{32}$
$(Me_4N)_4W_{10}O_{32}$
$(NISH^+)_nH_{(5-n)}BW_{12}O_{40}$
$(LYSH^+)_nH_{(5-n)}BW_{12}O_{40}$
$(ARGH^+)_nH_{(5-n)}BW_{12}O_{40}$
$(HISH^+)_nH_{(4-n)}SiW_{12}O_{40}$
$(LYSH^+)_nH_{(4-n)}SiW_{12}O_{40}$
$(ARGH^+)_nH_{(4-n)}SiW_{12}O_{40}$
a-$K_8SiW_{11}O_{39}$
a-$K_8SiW_{11}O_{39}$
$K_{10}(H_2W_{12}O_{42})$
$K_{12}Ni_3(II)(PW_9O_{34})_2 \cdot nH_2O$
$(NH_4)_{10}Co_4(II)(PW_9O_{34})_2 \cdot nH_2O$
$K_{12}Pd_3(II)(PW_9O_{34})_2 \cdot nH_2O$
$Na_{12}P_2W_{15}O_{56} \cdot 18H_2O$
$Na_{16}Cu_4(H_2O)_2(P_2W_{15}O_{56})_2 \cdot nH_2O$
$Na_{16}Zn_4(H_2O)_2(P_2W_{15}O_{56})_2 \cdot nH_2O$
$Na_{16}Co_4(H_2O)_2(P_2W_{15}O_{56})_2 \cdot nH_2O$
$Na_{16}Ni_4(H_2O)_2(P_2W_{15}O_{56})_2 \cdot nH_2O$
$Na_{16}Mn_4(H_2O)_2(P_2W_{15}O_{56}) \cdot nH_2O$
$Na_{16}Fe_4(H_2O)_2(P_2W_{15}O_{56})_2 \cdot nH_2O$
$K_{10}Zn_4(H_2O)_2(PW_9O_{34})_2 \cdot 20H_2O$
$K_{10}Ni_4(H_2O)_2(PW_9O_{34})_2 \cdot nH_2O$
$K_{10}Mn_4(H_2O)_2(PW_9O_{34})_2 \cdot nH_2O$
$K_{10}Fe_4(H_2O)_2(PW_9O_{34})_2 \cdot nH_2O$
$K_{12}Cu_3(PW_9O_{34})_2 \cdot nH_2O$
$K_{12}(Co\ H_2O)_3(PW_9O_{34})_2 \cdot nH_2O$
$K_{12}Zn_3(PW_9O_{34})_2 \cdot 15H_2O$
$K_{12}Mn_3(PW_9O_{34})_2 \cdot 15H_2O$
$K_{12}Fe_3(PW_9O_{34})_2 \cdot 25H_2O$
$(ARGH^+)_{10}(NH_4)_7Na[NaSb_9W_{21}O_{86}]$
$(ARGH^+)_5HW_{11}O_{39} \cdot 17H_2O$
$K_7Ti_2W_{10}O_{40}$
$[(CH_3)_4N]_7Ti_2W_{10}O_{40}$
$Cs_7Ti_2W_{10}O_{40}$
$[HISH+]_7Ti_2W_{10}O_{40}$
$(LYSH+)_nNa_{7-n}PTi_2W_{10}O_{40}$
$(ARGH+)_nNa_{7-n}PTi_2W_{10}O_{40}$
$Cs_4[SiW_{11}O_{39} \cdot O(SiCH_2CH_2C(O)OCH_3)_2]_4$—
$[TBA]_3H_3V_{10}O_{28}$
$K_7HNb_6O_{19} \cdot 13H_2O$
$K_8Ta_6O_{19} \cdot 17H_2O$
$[(CH_3)_4N^+]_4\ SiW_{11}O_{39}$—$O(SiCH_2CH_2C(O)OCH_3)_2$
$[CH_3)_4N^+]_4\ PW_{11}O_{39}$—$(SiCH_2CH_2CH_2CN)$
$[(CH_3)_4N^+]_4\ PW_{11}O_{39}$—$(SiCH_2CH_2CH_2Cl)$
$[(CH_3)_4N^+]_4\ PW_{11}O_{39}$—$(SiCH=CH_2)$
$Cs_4\ [SiW_{11}O_{39}$—$(SiCH_2CH_2CH_2CN)_2]$
$Cs_4\ [SiW_{11}O_{39}$—$(SiCH_2CH_2CH_2Cl)_2]$
$Cs_4\ [SiW_{11}O_{39}$—$(SiCH=CH_2)_2]$
$[(CH_3)_4N^+]_4SiW_{11}O_{39}O(SiCH_2CH_2CH_2CH_2CH_2CH_3)_2$
$[(CH_3)_4N^+]_4SiW_{11}$—$O_{39}O(SiCH_2CH_2CH_2Cl)_2$
$[(CH_3)_4N^+]_4SiW_{11}O_{39}$—$O(SiCH_2CH_2CH_2CN)_2$
$[(CH_3)_4N^+]SiW_{11}O_{39}$—$O(SiCH=CH_2)_2$
$[(CH_2)_4N^+]SiW_{11}O_{39}$—$O(SiC(CH_3)_3)_2$
$[(CH_3)_4N^+]SiW_{11}O_{39}$—$O(SiCH_2CH(CH_3)_2)_2$
$[(CH_3)_4N^+]_3PW_{11}O_{39}O(SiCH_2CH_2COOCH_3)_2$
$K_5Mn(II)PW_{11}O_{39}$—$nH_2O$
$K_8Mn(II)P_2W_{17}O_{61} \cdot nH_2O$
$K_6Mn(II)SiW_{11}O_{39} \cdot nH_2O$
$K_5PW_{11}O_{39}(SiMe_2) \cdot nH_2O$
$K_3PW_{11}O_{41}(PPh)_2 \cdot xH_2O$
$Na_3PW_{11}O_{41}(PPh)_2 \cdot xH_2O$
$K_5PTiW_{11}O_{40}$
$Cs_5PTiW_{11}O_{39}$
$K_6SiW_{11}O_{39}(SiMe_2) \cdot nH_2O$
$K_3PW_{11}O_{41}(PEt)_2 \cdot nH_2O$
$KSiW_{11}O_{39}[SiPh(t\text{-}Bu)] \cdot nH_2O$
$K_6SiW_{11}O_{39}(SiPh_2) \cdot nH_2O$
$K_7SiW_9Nb_3O_{40} \cdot nH_2O$
$Cs_7SiW_9Nb_3O_{40} \cdot nH_2O$
$Cs_8Si_2W_{18}Nb_6O_{77} \cdot nH_2O$
$(Me_3NH)_7SiW_9Nb_3O_{40} \cdot nH_2O$
$(CH_3H_6)_7SiW_9Nb_3O_{40} \cdot nH_2O$
$(CN_3H_6)_8Si_2W_{18}Nb_6O_{77} \cdot nH_2O$
$Rb_7SiW_9Nb_3O_{40} \cdot nH_2O$
$Rb_8Si_2W_{18}Nb_6O_{77} \cdot nH_2O$
$K_8Si_2W_{18}Nb_6O_{77} \cdot nH_2O$
$K_6P_2Mo_{18}O_{62} \cdot nH_2O$
$(C_5H_5N)_7HSi_2W_{18}Nb_6O_{77} \cdot nH_2O$
$(C_5H_5N)_7SiW_9Nb_3O_{40} \cdot nH_2O$
$(ARGH^+)_8\ SiW_{18}Nb_6O_{77} \cdot 18H_2O$ $(LYSH^+)_7K\ SiW_{18}Nb_6O_{77}.18H_2O$
$(HISH^+)_6K_2\ SiW_{18}Nb_6O_{77}.18H_2O$
$H_8Si_2W_{18}Nb_6O_{77}.nH_2O$ (2 batches)
$[(CH_3)_4N^+]_4SiW_{11}O_{39}—O(SiCH_2CH_3)_2$
$[(CH_3)_4N^+]_4SiW_{11}O_{39}—O(SiCH_3)_2$
$[(CH_3)_4N^+]_4SiW_{11}O_{39}—O(SiC_{16}H_{33})_2$
$Li_7HSi_2W_{18}Nb_6O_{77}$
$Li_9P_2V_3Me_3W_{12}O_{62}$
$Cs_9P_2V_3MeW_{12}O_{62}$
$Cs_{12}P_2V_3W_{12}O_{62}$
$K_4H_2PV_4W_8O_{40}$
$Na_{12}P_4W_{14}O_{58}$
$Na_{14}H_6P_6W_{18}O_{79}$
$a\text{-}K_5(NbO_2)SiW_{11}O_{39}$
$K_5(TaO_2)SiW_{11}O_{39}$
$(Me_3NH)_5(NbO_2)SiW_{11}O_{39}$
$(Me_3NH)_5NbSiW_{11}O_{40}$
$(Me_3NH)_5(TaO_2)SiW_{11}O_{39}$
$K_4(NbO_2)PW_{11}O_{39}$
$K_7(NbO_2)P_2W_{12}O_{61}$
$(Me_3NH)_7(NbO_2)_3SiW_9O_{37}$
$Cs_7(NbO_2)_3SiW_9O_{37}$
$K_6(NbO_2)_3PW_9O_{37}$
$Na_{10}(H_2W_{12}O_{42})$
$K_4NbPW_{11}O_{40}$
$(Me_3NH)_4NbPW_{11}O_{40}$
$K_5NbSiW_{11}O_{40}$
$K_5TaSiW_{11}O_{40}$
$(Me_3NH)_5TaSiW_{11}O_{40}$
$K_6Nb_3PW_9O_{40}$
$K_7NbP_2W_{17}O_{62}$
$K_7(TiO_2)_2PW_{10}O_{38}$
$K_7(TaO_2)_3SiW_9O_{37}$
$K_7Ta_3SiW_9O_{40}$
$K_6(TaO_2)_3PW_9O_{37}$
$K_6Ta_3PW_9O_{40}$
$K_8Co_2W_{11}O_{39}$
$H_2(Me_4N)_4(EtSi)_2CoW_{11}O_{40}$
$H_2(Me_4N)_4(iso\text{-}C_4H_9Si)_2CoW_{11}O_{40}$
$K_9(NbO_2)_3P_2W_{15}O_{59}$
$K_9Nb_3P_2W_{15}O_{62}$
$K_{12}(NbO_2)_6P_2W_{12}O_{56}$
$K_{12}Nb_6P_2W_{12}O_{61}$
$a_2\text{-}K_{10}P_2W_{17}O_{61}$
$K_6Fe(III)Nb_3P_2W_{15}O_{62}$
$K_7Zn(II)Nb_3P_2W_{15}O_{62}$
$(NH_4)_6[a\text{-}P_2W_{18}O_{62}].nH_2O$
$K_{12}[H_2P_2W_{12}O_{48}].24H_2O$
$K_{12}[H_2P_2W_{12}O_{48}].24H_2O$
$K_2Na_{1.5}H_{4.5}[PtMo_6O_{24}].8H_2O$
$K_6[a_2\text{-}P_2W_{17}MoO_{62}].nH_2O$
$KHP_2V_3W_{15}O_{62}.34H_2O$
$K_6[P_2W_{12}Nb_6O_{62}].24H_2O$
$Na_6[V_{10}O_{28}].18H_2O$
$(Guanidinium)_8H[PV_{14}O_{62}].3H_2O$
$K_8H[PV_{14}O_{62}]$ $Na_7[MnV_{13}O_{38}].18H_2O$
$K_6[BW_{11}O_{39}Ga(OH_2)].13H_2O$
$K_7H[Nb_6O_{19}].13H_2O$
$K_7H[Nb_6O_{19}].13H_2O$
$[MeN/Na/K]_4[Nb_2W_4O_{19}]$
$[Me_4N]_9[P_2W_{15}Nb_3P_{62}]$
$[Me_4N]_{15}[HP_4W_{30}Nb_6O_{123}].16H_2O$
$[Me_4N]_{15}[HP_4W_{30}Nb_6O_{123}].16H_2O$
$[Na/K]_6Nb_4W_2O_{19}]$
$[Me_4N/Na/K]_5[Nb_3W_3O_{19}].6H_2O$
$[Me_4N/Na/K]_5[Nb_3W_3O_{19}].6H_2O$
$[Me_5CpRh]_4V_6O_{19}]$
$K_5[CpTiSiW_{11}O_{39}].12H_2O$
$b_2\text{-}K_8[SiW_{11}O_{39}].14H_2O$
$a\text{-}K_8[SiW_{10}O_{36}].12H_2O$
$Cs_7Na_2[PW_{10}O_{37}].8H_2O$
$Cs_6[P_2W_5O_{23}].7(½)H_2O$
$g\text{-}Cs_7[PW_{10}O_{36}].7H_2O$
$K_5[SiNbW_{11}O_{40}].7H_2O$
$K_4[PNbW_{11}O_{40}].12H_2O$
$Na_6[Nb_4W_2O_{19}].13H_2O$
$Na_6[Nb_4W_2O_{19}].20H_2O$
$K_6[Nb_4W_2O_{19}].7H_2O$
$K_4[V_2W_4O_{19}].3.5H_2O$
$Na_5[V_3W_3O_{19}].12H_2O$
$K_6[PV_3W_9O_{40}].14H_2O$
$Na_9[A\text{-}b\text{-}GeW_9O_{34}].8H_2O$
$Na_{10}[A\text{-}a\text{-}GeW_9O_{34}].9H_2O$
$K_7[BV_2W_{10}O_{40}].6H_2O$
$Na_5[CH_3Sn(Nb_6O_{19})].10H_2O$
$Na_5[CH_3Sn(Nb_6O_{19})].10H_2O$
$Na_8[Pt(P(m\text{-}SO_3Ph)_3)_3Cl].3H_2O$
$Na_3[P(m\text{-}SO_3Ph)_3].H_2O$
$(Me_3NH)_{10}(H)[Si_2(ZrOH)_3W_{18}O_{68}].10H_2O$
$(Me_3NH)_{10}(H)[Si_2(ZrOH)_3W_{18}O_{68}].10H_2O$
$K_7[A\text{-}a\text{-}GeNb_3W_9O_{40}].18H_2O$
$K_7[A\text{-}b\text{-}SiNb_3W_9O_{40}].20H_2O$
$(Me_3NH)_9[A\text{-}a\text{-}HSi_2Nb_6W_{18}O_{78}]$
$(Me_3NH)_9[A\text{-}a\text{-}HGe_2Nb_6W_{18}O_{78}]$
$(Me_3NH)_9[A\text{-}a\text{-}HGe_2Nb_6W_{18}O_{78}]$
$K_7(H)[A\text{-}a\text{-}Ge_2Nb_6W_{18}O_{77}].18H_2O$
$K_8[A\text{-}b\text{-}Si_2Nb_6W_{18}O_{77}]$ and
$(Me_3NH)_8[A\text{-}b\text{-}Si_2Nb_6W_{18}O_{77}]$.

2. The method of claim 1, wherein said polyoxometalate is selected from the group consisting of $Na_{17}P_7W_{15}O_{56}.18H_2O$, $Na_{16}Mn_4(H_2O)_2(P_2W_{15}O_{56}).nH_2O$, $K_{10}Mn_4(H_2O)_2(PW_9O_{34})_2.nH_2O$, $K_{10}Fe_4(H_2O)_2(PW_9O_{34})_2.nH_2O$, $(Me_3NH)_7SiW_9NbO_{40}.nH_2O$, $(Me_3NH)_5(NbO_2)SiW_{11}O_{39}$, $H_2(Me_4N)_4(EtSi)_2CoW_{11}O_{40}$, and $K_8(A\text{-}\beta\text{-}Si_2Nb_6W_{18}O_{77})$.

3. The method of claim 1, wherein said polyoxometalate is $K_{10}Fe_4(H_2O)_2(PW_9O_{34})_2n.H_2O$.

4. The method of claim 1, wherein said respiratory viral infection is influenza A, influenza B, or RSV.

5. The method of claim 1, wherein said polyoxometalate is administered in the form of an aerosol.

6. The method of claim 1, wherein said polyoxometalate is $K_8(A\text{-}\beta\text{-}Si_2Nb_6W_{18}O_{77})$.

7. A method for treating herpes virus infection, comprising administering to a patient in need thereof an effective amount of a polyoxometalate selected from the group consisting of

[(NMP)$_2$H]$_3$PW$_{12}$O$_{40}$
[(DMA)$_2$H]$_3$PMo$_{12}$O$_{40}$
(NH$_4$)$_{17}$Na[NaSb$_9$W$_{21}$O$_{86}$]
a- and b-H$_5$BW$_{12}$O$_{40}$
a- and b-H$_6$ZnW$_{12}$O$_{40}$
a- and b-H$_6$P$_2$W$_{18}$O$_{62}$
α-(NH$_4$)$_6$P$_2$W$_{18}$O$_{62}$
K$_{10}$Cu$_4$(H$_2$O)$_2$(PW$_9$O$_{34}$)$_2$·20H$_2$O
K$_{10}$Co$_4$(H$_2$O)$_2$(PW$_9$O$_{34}$)$_2$·20H$_2$O
Na$_7$PW$_{11}$O$_{39}$
Na$_7$PW$_{11}$O$_{39}$·20H$_2$O+2C$_6$H$_5$P(O)(OH)$_2$
(n-Bu$_4$N)$_4$H$_3$PW$_{11}$O$_{39}$
b-Na$_8$HPW$_9$O$_{34}$
(n-Bu$_4$N)$_3$PMoW$_{11}$O$_{39}$
a-[(nBu)$_4$N]$_4$Mo$_8$O$_{26}$
(n-Bu$_4$N)$_2$W$_6$O$_{19}$
(n-Bu$_4$N)$_2$Mo$_6$O$_{19}$
a-(NH$_4$)$_n$H$_{(4-n)}$SiW$_{12}$O$_{40}$
a-(NH$_4$)$_n$H$_{(5-n)}$BW$_{12}$O$_{40}$
a-K$_5$BW$_{12}$O$_{40}$
K$_4$W$_4$O$_{10}$(O$_2$)6
b-Na$_9$HSiW$_9$O$_{34}$
Na$_6$H$_2$W$_{12}$O$_{40}$
(NH$_4$)$_{14}$[NaP$_5$W$_{30}$O$_{110}$]
a-(NH$_4$)$_5$BW$_{12}$O$_{40}$
a-Na$_5$BW$_{12}$O$_{40}$
(NH$_4$)$_4$W$_{10}$O$_{32}$
(Me$_4$N)$_4$W$_{10}$O$_{32}$
(HISH$^+$)$_n$H$_{(5-n)}$BW$_{12}$O$_{40}$
(LYSH$^+$)$_n$H$_{(5-n)}$BW$_{12}$O$_{40}$
(ARGH$^+$)$_n$H$_{(5-n)}$BW$_{12}$O$_{40}$
(HISH$^+$)$_n$H$_{(4-n)}$SiW$_{12}$O$_{40}$
(LYSH$^+$)$_n$H$_{(4-n)}$SiW$_{12}$O$_{40}$
(ARGH$^+$)$_n$H$_{(4-n)}$SiW$_{12}$O$_{40}$
a-K$_8$SiW$_{11}$O$_{39}$
a-K$_8$SiW$_{11}$O$_{39}$
K$_{10}$(H$_2$W$_{12}$O$_{42}$)
K$_{12}$Ni$_3$(II)(PW$_9$O$_{34}$)$_2$·$n$H$_2$O
(NH$_4$)$_{10}$Co$_4$(II)(PW$_9$O$_{34}$)$_2$·$n$H$_2$O
K$_{12}$Pd$_3$(II)(PW$_9$O$_{34}$)$_2$·$n$H$_2$O
Na$_{12}$P$_2$W$_{15}$O$_{56}$·18H$_2$O
Na$_{16}$Cu$_4$(H$_2$O)$_2$(P$_2$W$_{15}$O$_{56}$)$_2$·$n$H$_2$O
Na$_{16}$Zn$_4$(H$_2$O)$_2$(P$_2$W$_{15}$O$_{56}$)$_2$·$n$H$_2$O
Na$_{16}$Co$_4$(H$_2$O)$_2$(P$_2$W$_{15}$O$_{56}$)$_2$·$n$H$_2$O
Na$_{16}$Ni$_4$(H$_2$O)$_2$(P$_2$W$_{15}$O$_{56}$)$_2$·$n$H$_2$O
Na$_{16}$Mn$_4$(H$_2$O)$_2$(P$_2$W$_{15}$O$_{56}$)$_2$·$n$H$_2$O
Na$_{16}$Fe$_4$(H$_2$O)$_2$(P$_2$W$_{15}$O$_{56}$)$_2$·$n$H$_2$O
K$_{10}$Zn$_4$(H$_2$O)$_2$(PW$_9$O$_{34}$)$_2$·20H$_2$O
K$_{10}$Ni$_4$(H$_2$O)$_2$(PW$_9$O$_{34}$)$_2$·$n$H$_2$O
K$_{10}$Mn$_4$(H$_2$O)$_2$(PW$_9$O$_{34}$)$_2$·$n$H$_2$O
K$_{10}$Fe$_4$(H$_2$O)$_2$(PW$_9$O$_{34}$)$_2$·$n$H$_2$O
K$_{12}$Cu$_3$(PW$_9$O$_{34}$)$_2$·$n$H$_2$O
K$_{12}$(Co H$_2$O)$_3$(PW$_9$O$_{34}$)$_2$·$n$H$_2$O
K$_{12}$Zn$_3$(PW$_9$O$_{34}$)$_2$·15H$_2$O
K$_{12}$Mn$_3$(PW$_9$O$_{34}$)$_2$·15H$_2$O
K$_{12}$Fe$_3$(PW$_9$O$_{34}$)$_2$·25H$_2$O (ARGH$^+$)$_{10}$(NH$_4$)$_7$Na[NaSb$_9$W$_{21}$O$_{86}$]
(ARGH$^+$)$_5$HW$_{11}$O$_{39}$·17H$_2$O
K$_7$Ti$_2$W$_{10}$O$_{40}$
[(CH$_3$)$_4$N]$_7$Ti$_2$W$_{10}$O$_{40}$
Cs$_7$Ti$_2$W$_{10}$O$_{40}$
[HISH+]$_7$Ti$_2$W$_{10}$O$_{40}$
(LYSH+)$_n$Na$_{7-n}$PTi$_2$W$_{10}$O$_{40}$
(ARGH+)$_n$Na$_{7-n}$PTi$_2$W$_{10}$O$_{40}$
Cs$_4$[SiW$_{11}$O$_{39}$·O(SiCH$_2$CH$_2$C(O)OCH$_3$)$_2$]$_4$—
[TBA]$_3$H$_3$V$_{10}$O$_{28}$
K$_7$HNb$_6$O$_{19}$·13H$_2$O
K$_8$Ta$_6$O$_{19}$·17H$_2$O
[(CH$_3$)$_4$N$^+$]$_4$SiW$_{11}$O$_{39}$—O(SiCH$_2$CH$_2$C(O)OCH$_3$)$_2$
[CH$_3$)$_4$N$^+$]$_4$PW$_{11}$O$_{39}$—(SiCH$_2$CH$_2$CH$_2$CN)
[(CH$_3$)$_4$N$^+$]$_4$PW$_{11}$O$_{39}$—(SiCH$_2$CH$_2$CH$_2$Cl)
[(CH$_3$)$_4$N$^+$]$_4$PW$_{11}$O$_{39}$—(SiCH=CH$_2$)
Cs$_4$[SiW$_{11}$O$_{39}$—(SiCH$_2$CH$_2$CH$_2$CN)$_2$]
Cs$_4$[SiW$_{11}$O$_{39}$—(SiCH$_2$CH$_2$CH$_2$Cl)$_2$]
Cs$_4$[SiW$_{11}$O$_{39}$—(SiCH=CH$_2$)$_2$]
[(CH$_3$)$_4$N$^+$]$_4$SiW$_{11}$O$_{39}$O(SiCH$_2$CH$_2$CH$_2$CH$_2$CH$_2$CH$_3$)$_2$
[(CH$_3$)$_4$N$^+$]$_4$SiW$_{11}$O$_{39}$—O(SiCH$_2$CH$_2$CH$_2$Cl)$_2$
[(CH$_3$)$_4$N$^+$]$_4$SiW$_{11}$O$_{39}$—O(SiCH$_2$CH$_2$CH$_3$CN)$_2$
[(CH$_3$)$_4$N$^+$]SiW$_{11}$O$_{39}$—O(SiCH=CH$_2$)$_2$
[(CH$_2$)$_4$N$^+$]SiW$_{11}$O$_{39}$—O(SiC(CH$_3$)$_3$)$_2$
[(CH$_3$)$_4$N$^+$]SiW$_{11}$O$_{39}$—O(SiCH$_2$CH(CH$_3$)$_2$)$_2$
[(CH$_3$)$_4$N$^+$]$_3$PW$_{11}$O$_{39}$O(SiCH$_2$CH$_2$COOCH$_3$)$_2$
K$_5$Mn(II)PW$_{11}$O$_{39}$·$n$H$_2$O
K$_8$Mn(II)P$_2$W$_{17}$O$_{61}$·$n$H$_2$O
K$_6$Mn(II)SiW$_{11}$O$_{39}$·$n$H$_2$O
K$_5$PW$_{11}$O$_{39}$(SiMe$_2$)·$n$H$_2$O
K$_3$PW$_{11}$O$_{41}$(PPh)$_2$·$x$H$_2$O
Na$_3$PW$_{11}$O$_{41}$(PPh)$_2$·$x$H$_2$O
K$_5$PTiW$_{11}$O$_{40}$
Cs$_5$PTiW$_{11}$O$_{39}$
K$_6$SiW$_{11}$O$_{39}$(SiMe$_2$)·$n$H$_2$O
K$_3$PW$_{11}$O$_{41}$(PEt)$_2$·$n$H$_2$O
KSiW$_{11}$O$_{39}$[SiPh(t-Bu)]·$n$H$_2$O
K$_6$SiW$_{11}$O$_{39}$(SiPh$_2$)·$n$H$_2$O
K$_7$SiW$_9$Nb$_3$O$_{40}$·$n$H$_2$O
Cs$_7$SiW$_9$Nb$_3$O$_{40}$·$n$H$_2$O
Cs$_8$Si$_2$W$_{18}$Nb$_6$O$_{77}$·$n$H$_2$O
(Me$_3$NH)$_7$SiW$_9$Nb$_3$O$_{40}$·$n$H$_2$O
(CN$_3$H$_6$)$_7$SiW$_9$Nb$_3$O$_{40}$·$n$H$_2$O
(CN$_3$H$_6$)$_8$Si$_2$W$_{18}$Nb$_6$O$_{77}$·$n$H$_2$O
Rb$_7$SiW$_9$Nb$_3$O$_{40}$·$n$H$_2$O
Rb$_8$Si$_2$W$_{18}$Nb$_6$O$_{77}$·$n$H$_2$O
K$_8$Si$_2$W$_{18}$Nb$_6$O$_{77}$·$n$H$_2$O
K$_6$P$_2$Mo$_{18}$O$_{62}$·$n$H$_2$O
(C$_5$H$_5$N)$_7$HSi$_2$W$_{18}$Nb$_6$O$_{77}$·$n$H$_2$O
(C$_5$H$_5$N)$_7$SiW$_9$Nb$_3$O$_{40}$·$n$H$_2$
(ARGH$^+$)$_8$SiW$_{18}$Nb$_6$O$_{77}$·18H$_2$O
(LYSH$^+$)$_7$K SiW$_{18}$Nb$_6$O$_{77}$·18H$_2$O
(HISH$^+$)$_6$K$_2$SiW$_{18}$Nb$_6$O$_{77}$·18H$_2$O
H$_8$Si$_2$W$_{18}$Nb$_6$O$_{77}$·$n$H$_2$O (2batches)
[(CH$_3$)$_4$N$^+$]$_4$SiW$_{11}$O$_{39}$—O(SiCH$_2$CH$_3$)$_2$
[(CH$_3$)$_4$N$^+$]$_4$SiW$_{11}$O$_{39}$—O(SiCH$_3$)$_2$

[(CH$_3$)$_4$H$^+$]$_4$SiW$_{11}$O$_{39}$—O(SiC$_{16}$H$_{33}$)$_2$
Li$_7$HSi$_2$W$_{18}$Nb$_6$O$_{77}$
Li$_9$P$_2$V$_3$Me$_3$W$_{12}$O$_{62}$
Cs$_9$P$_2$V$_3$MeW$_{12}$O$_{62}$
Cs$_{12}$P$_2$V$_3$W$_{12}$O$_{62}$
K$_4$H$_2$PV$_4$W$_8$O$_{40}$
Na$_{12}$P$_4$W$_{14}$O$_{58}$
Na$_{14}$H$_6$P$_6$W$_{18}$O$_{79}$
a-K$_5$(NbO$_2$)SiW$_{11}$O$_{39}$
K$_5$(TaO$_2$)SiW$_{11}$O$_{39}$
(Me$_3$NH)$_5$(NbO$_2$)SiW$_{11}$O$_{39}$
(Me$_3$NH)$_5$NbSiW$_{11}$O$_{40}$
(Me$_3$NH)$_5$(TaO$_2$)SiW$_{11}$O$_{39}$
K$_4$(NbO$_2$)PW$_{11}$O$_{39}$
K$_7$(NbO$_2$)P$_2$W$_{12}$O$_{61}$
(Me$_3$NH)$_7$(NbO$_2$)$_3$SiW$_9$O$_{37}$
Cs$_7$(NbO$_2$)$_3$SiW$_9$O$_{37}$
K$_6$(NbO$_2$)$_3$PW$_9$O$_{37}$
Na$_{10}$(H$_2$W$_{12}$O$_{42}$)
K$_4$NbPW$_{11}$O$_{40}$
(Me$_3$NH)$_4$NbPW$_{11}$O$_{40}$
K$_5$NbSiW$_{11}$O$_{40}$
K$_5$TaSiW$_{11}$O$_{40}$
(Me$_3$NH)$_5$TaSiW$_{11}$O$_{40}$
K$_6$Nb$_3$PW$_9$O$_{40}$
K$_7$NbP$_2$W$_{17}$O$_{62}$
K$_7$(TiO$_2$)$_2$PW$_{10}$O$_{38}$
K$_7$(TaO$_2$)$_3$SiW$_9$O$_{37}$
K$_7$Ta$_3$SiW$_9$O$_{40}$
K$_6$(TaO$_2$)$_3$PW$_9$O$_{37}$
K$_6$Ta$_3$PW$_9$O$_{40}$
K$_8$Co$_2$W$_{11}$O$_{39}$
H$_2$(Me$_4$N)$_4$(EtSi)$_2$CoW$_{11}$O$_{40}$
H$_2$(Me$_4$N)$_4$(iso-C$_4$H$_9$Si)$_2$CoW$_{11}$O$_{40}$
K$_9$(NbO$_2$)$_3$P$_2$W$_{15}$O$_{59}$
K$_9$Nb$_3$P$_2$W$_{15}$O$_{62}$
K$_{12}$(NbO$_2$)$_6$P$_2$W$_{12}$O$_{56}$
K$_{12}$Nb$_6$P$_2$W$_{12}$O$_{62}$
a$_2$-K$_{10}$P$_2$W$_{17}$O$_{61}$
K$_6$Fe(III)Nb$_3$P$_2$W$_{15}$O$_{62}$
K$_7$Zn(II)Nb$_3$P$_2$W$_{15}$O$_{62}$
(NH$_4$)$_6$[a-P$_2$W$_{18}$O$_{62}$].$n$H$_2$O
K$_{12}$[H$_2$P$_2$W$_{12}$O$_{48}$].24H$_2$O
K$_{12}$[H$_2$P$_2$W$_{12}$O$_{48}$].24H$_2$O
K$_2$Na$_{1.5}$H$_{4.5}$(PtMo$_6$O$_{24}$).8H$_2$O
K$_6$[a$_2$-P$_2$W$_{17}$MoO$_{62}$].$n$H$_2$O
KHP$_2$V$_3$W$_{15}$O$_{62}$.3H$_2$O
K$_6$[P$_2$W$_{12}$Nb$_6$O$_{62}$].24H$_2$O
Na$_6$[V$_{10}$O$_{28}$].18H$_2$O
(Guanidinium)$_8$H[PV$_{14}$O$_{62}$].3H$_2$O
K$_8$H[PV$_{14}$O$_{62}$]
Na$_7$[MnV$_{13}$O$_{38}$].18H$_2$O
K$_6$[BW$_{11}$O$_{39}$Ga(OH$_2$)].13H$_2$O
K$_7$H[Nb$_6$O$_{19}$].13H$_2$O
K$_7$H[Nb$_6$O$_{19}$].13H$_2$O
[MeN/Na/K]$_4$[Nb$_2$W$_4$O$_{19}$]

[Me$_4$N]$_9$[P$_2$W$_{15}$Nb$_3$P$_{62}$]
[Me$_4$N]$_{15}$[HP$_4$W$_{30}$Nb$_6$O$_{123}$].16H$_2$O
[Me$_4$N]$_{15}$[HP$_4$W$_{30}$Nb$_6$O$_{123}$].16H$_2$O
[Na/K]$_6$Nb$_4$W$_2$O$_{19}$]
[Me$_4$N/Na/K]$_5$[Nb$_3$W$_3$O$_{19}$].6H$_2$O
[Me$_4$N/Na/K]$_5$[Nb$_3$W$_3$O$_{19}$].6H$_2$O
[Me$_5$CpRh]$_4$V$_6$O$_{19}$]
K$_5$[CpTiSiW$_{11}$O$_{39}$].12H$_2$O
b$_2$-K$_8$[SiW$_{11}$O$_{39}$].14H$_2$O
a-K$_8$[SiW$_{10}$O$_{36}$].12H$_2$O
Cs$_7$Na$_2$[PW$_{10}$O$_{37}$].8H$_2$O
Cs$_6$[P$_2$W$_5$O$_{23}$].7(½)H$_2$O
g-Cs$_7$[PW$_{10}$O$_{36}$].7H$_2$O
K$_5$[SiNbW$_{11}$O$_{40}$].7H$_2$O
K$_4$[PNbW$_{11}$O$_{40}$].12H$_2$O
Na$_6$[Nb$_4$W$_2$O$_{19}$].13H$_2$O
Na$_6$[Nb$_4$W$_2$O$_{19}$].20H$_2$O
K$_6$[Nb$_4$W$_2$O$_{19}$].7H$_2$O
K$_4$[V$_2$W$_4$O$_{19}$].3.5H$_2$O
Na$_5$[V$_3$W$_3$O$_{19}$].12H$_2$O
K$_6$[PV$_3$W$_9$O$_{40}$].14H$_2$O
Na$_9$[A-b-GeW$_9$O$_{34}$].8H$_2$O
Na$_{10}$[A-a-GeW$_9$O$_{34}$].9H$_2$O
K$_7$[BV$_2$W$_{10}$O$_{40}$].6H$_2$O
Na$_5$[CH$_3$Sn(Nb$_6$O$_{19}$)].10H$_2$O
Na$_5$[CH$_3$Sn(Nb$_6$O$_{19}$)].10H$_2$O
Na$_8$[Pt(P(m-SO$_3$Ph)$_3$)$_3$Cl].3H$_2$O
Na$_3$[P(m-SO$_3$Ph)$_3$].H$_2$O
(Me$_3$NH)$_{10}$(H)[Si$_2$(ZrOH)$_3$W$_{18}$O$_{68}$].10H$_2$O
(Me$_3$NH)$_{10}$(H)[Si$_2$(ZrOH)$_3$W$_{18}$O$_{68}$].10H$_2$O
K$_7$[A-a-GeNb$_3$W$_9$O$_{40}$].18H$_2$O
K$_7$[A-b-SiNb$_3$W$_9$O$_{40}$].20H$_2$O
(Me$_3$NH)$_9$[A-a-HSi$_2$Nb$_6$W$_{18}$O$_{78}$]
(Me$_3$NH)$_9$[A-a-HGe$_2$Nb$_6$W$_{18}$O$_{78}$]
(Me$_3$NH)$_9$[A-a-HGe$_2$Nb$_6$W$_{18}$O$_{78}$]
K$_7$(H)[A-a-Ge$_2$Nb$_6$W$_{18}$O$_{77}$].18H$_2$O
K$_8$[A-b-Si$_2$Nb$_6$W$_{18}$O$_{77}$] and
(Me$_3$NH)$_8$[A-b-Si$_2$Nb$_6$W$_{18}$O$_{77}$].

8. The method of claim 7, wherein said herpesvirus is selected from the group consisting of herpes simplex virus type 1, herpes simplex virus type 2, cytomegalovirus, Epstein-Barr virus, human herpesvirus type 6, human herpesvirus type 7, and human herpesvirus type 8.

9. The method of claim 7, wherein said polyoxometalate is K$_8$(A-β-Si$_2$Nb$_6$W$_{18}$O$_{77}$).

10. A method for treating hepadnavirus infection, comprising administering to a patient in need thereof an effective amount of a polyoxometalate selected from the group consisting of

[(NMP)$_2$H]$_3$PW$_{12}$O$_{40}$
[(DMA)$_2$H]$_3$PMo$_{12}$O$_{40}$
(NH$_4$)$_{17}$Na[NaSb$_9$W$_{21}$O$_{86}$]
a- and b-H$_5$BW$_{12}$O$_{40}$
a- and b-H$_6$ZnW$_{12}$O$_{40}$
a- and b-H$_6$P$_2$W$_{18}$O$_{62}$
α-(NH$_4$)$_6$P$_2$W$_{18}$O$_{62}$
K$_{10}$Cu$_4$(H$_2$O)$_2$(PW$_9$O$_{34}$)$_2$.20H$_2$O
K$_{10}$Co$_4$(H$_2$O)$_2$(PW$_9$O$_{34}$)$_2$.20H$_2$O $Na_7PW_{11}O_{39}$
$Na_7PW_{11}O_{39} \cdot 20H_2O + 2C_6H_5P(O)(OH)_2$
$(n\text{-}Bu_4N)_4H_3PW_{11}O_{39}$
$b\text{-}Na_8HPW_9O_{34}$
$(n\text{-}Bu_4N)_3PMoW_{11}O_{39}$
$a\text{-}[(nBu)_4N]_4Mo_8O_{26}$
$(n\text{-}Bu_4N)_2W_6O_{19}$
$(n\text{-}Bu_4N)_2Mo_6O_{19}$
$a\text{-}(NH_4)_nH_{(4-n)}SiW_{12}O_{40}$
$a\text{-}(NH_4)_nH_{(5-n)}BW_{12}O_{40}$
$a\text{-}K_5BW_{12}O_{40}$
$K_4W_4O_{10}(O_2)6$
$b\text{-}Na_9HSiW_9O_{34}$
$Na_6H_2W_{12}O_{40}$
$(NH_4)_{14}[NaP_5W_{30}O_{110}]$
$a\text{-}(NH_4)_5BW_{12}O_{40}$
$a\text{-}Na_5BW_{12}O_{40}$
$(NH_4)_4W_{10}O_{32}$
$(Me_4N)_4W_{10}O_{32}$
$(HISH^+)_nH_{(5-n)}BW_{12}O_{40}$
$(LYSH^+)_nH_{(5-n)}BW_{12}O_{40}$
$(ARGH^+)_nH_{(5-n)}BW_{12}O_{40}$
$(HISH^+)_nH_{(4-n)}SiW_{12}O_{40}$
$(LYSH^+)_nH_{(4-n)}SiW_{12}O_{40}$
$(ARGH^+)_nH_{(4-n)}SiW_{12}O_{40}$
$a\text{-}K_8SiW_{11}O_{39}$
$a\text{-}K_8SiW_{11}O_{39}$
$K_{10}(H_2W_{12}O_{42})$
$K_{12}Ni_3(II)(PW_9O_{34})_2 \cdot nH_2O$
$(NH_4)_{10}Co_4(II)(PW_9O_{34})_2 \cdot nH_2O$
$K_{12}Pd_3(II)(PW_9O_{34})_2 \cdot nH_2O$
$Na_{12}P_2W_{15}O_{56} \cdot 18H_2O$
$Na_{16}Cu_4(H_2O)_2(P_2W_{15}O_{56})_2 \cdot nH_2O$
$Na_{16}Zn_4(H_2O)_2(P_2W_{15}O_{56})_2 \cdot nH_2O$
$Na_{16}Co_4(H_2O)_2(P_2W_{15}O_{56})_2 \cdot nH_2O$
$Na_{16}Ni_4(H_2O)_2(P_2W_{15}O_{56})_2 \cdot nH_2O$
$Na_{16}Mn_4(H_2O)_2(P_2W_{15}O_{56})nH_2O$
$Na_{16}Fe_4(H_2O)_2(P_2W_{15}O_{56})_2 \cdot nH_2O$
$K_{10}Zn_4(H_2O)_2(PW_9O_{34})_2 \cdot 20H_2O$
$K_{10}Ni_4(H_2O)_2(PW_9O_{34})_2 \cdot nH_2O$
$K_{10}Mn_4(H_2O)_2(PW_9O_{34})_2 \cdot nH_2O$
$K_{10}Fe_4(H_2O)_2(PW_9O_{34})_2 \cdot nH_2O$
$K_{12}Cu_3(PW_9O_{34})_2 \cdot nH_2O$
$K_{12}(Co\ H_2O)_3(PW_9O_{34})_2 \cdot nH_2O$
$K_{12}Zn_3(PW_9O_{34})_2 \cdot 15H_2O$
$K_{12}Mn_3(PW_9O_{34})_2 \cdot 15H_2O$
$K_{12}Fe_3(PW_9O_{34})_2 \cdot 25H_2O$
$(ARGH^+)_{10}(NH_4)_7\ Na[NaSb_9W_{21}O_{86}]$
$(ARGH^+)_5HW_{11}O_{39} \cdot 17H_2O$
$K_7Ti_2W_{10}O_{40}$
$[(CH_3)_4N]_7Ti_2W_{10}O_{40}$
$Cs_7Ti_2W_{10}O_{40}$
$[HISH+]_7Ti_2W_{10}O_{40}$
$(LYSH+)_nNa_{7-n}PTi_2W_{10}O_{40}$
$(ARGH+)_nNa_{7-n}PTi_2W_{10}O_{40}$
$Cs_4[SiW_{11}O_{39} \cdot O(SiCH_2CH_2C(O)OCH_3)_2]_4$—

$[TBA]_3H_3V_{10}O_{28}$
$K_7HNb_6O_{19} \cdot 13H_2O$
$K_8Ta_6O_{19} \cdot 17H_2O$
$[(CH_3)_4N^+]_4SiW_{11}O_{39}\text{—}O(SiCH_2CH_2C(O)OCH_3)_2$
$[CH_3)_4N^+]_4PW_{11}O_{39}\text{—}(SiCH_2CH_2CH_2CN)$
$[(CH_3)_4N^+]_4PW_{11}O_{39}\text{—}(SiCH_2CH_2CH_2Cl)$
$[(CH_3)_4N^+]_4PW_{11}O_{39}\text{—}(SiCH=CH_2)$
$Cs_4[SiW_{11}O_{39}\text{—}(SiCH_2CH_2CH_2CN)_2]$
$Cs_4[SiW_{11}O_{39}\text{—}(SiCH_2CH_2CH_2Cl)_2]$
$Cs_4[SiW_{11}O_{39}\text{—}(SiCH=CH_2)_2]$
$[(CH_3)_4N^+]_4SiW_{11}O_{39}O(SiCH_2CH_2CH_2CH_2CH_2CH_3)_2$
$[(CH_3)_4N^+]_4SiW_{11}O_{39}\text{—}O(SiCH_2CH_2CH_2Cl)_2$
$[(CH_3)_4N^+]_4SiW_{11}O_{39}\text{—}O(SiCH_2CH_2CH_2CN)_2$
$[(CH_3)_4N^+]SiW_{11}O_{39}\text{—}O(SiCH=CH_2)_2$
$[(CH_2)_4N^+]SiW_{11}O_{39}\text{—}O(SiC(CH_3)_3)_2$
$[(CH_3)_4N^+]SiW_{11}O_{39}\text{—}O(SiCH_2CH(CH_3)_2)_2$
$[(CH_3)_4N^+PW_{11}O_{39}O(SiCH_2CH_2COOCH_3)_2$
$K_5Mn(II)PW_{11}O_{39} \cdot nH_2O$
$K_8Mn(II)P_2W_{17}O_{61} \cdot nH_2O$
$K_6Mn(II)SiW_{11}O_{39} \cdot nH_2O$
$K_5PW_{11}O_{39}(SiMe_2) \cdot nH_2O$
$K_3PW_{11}O_{41}(PPh)_2 \cdot xH_2O$
$Na_3PW_{11}O_{41}(PPh)_2 \cdot xH_2O$
$K_5PTiW_{11}O_{40}$
$Cs_5PTiW_{11}O_{39}$
$K_6SiW_{11}O_{39}(SiMe_2) \cdot nH_2O$
$K_3PW_{11}O_{41}(PEt)_2 \cdot nH_2O$
$KSiW_{11}O_{39}[SiPh(t\text{-}Bu)] \cdot nH_2O$
$K_6SiW_{11}O_{39}(SiPh_2) \cdot nH_2O$
$K_7SiW_9Nb_3O_{40} \cdot nH_2O$
$Cs_7SiW_9Nb_3O_{40} \cdot nH_2O$
$Cs_8Si_2W_{18}Nb_6O_{77} \cdot nH_2O$
$(Me_3NH)_7SiW_9Nb_3O_{40} \cdot nH_2O$
$(CN_3H_6)_7SiW_9Nb_3O_{40} \cdot nH_2O$
$(CN_3H_6)_8Si_2W_{18}Nb_6O_{77} \cdot nH_2O$
$Rb_7SiW_9Nb_3O_{40} \cdot nH_2O$
$Rb_8Si_2W_{18}Nb_6O_{77} \cdot nH_2O$
$K_8Si_2W_{18}Nb_6O_{77} \cdot nH_2O$
$K_6P_2Mo_{18}O_{62} \cdot nH_2O$
$(C_5H_5N)_7HSi_2W_{18}Nb_6O_{77} \cdot nH_2O$
$(C_5H_5N)_7SiW_9Nb_3O_{40} \cdot nH_2O$
$(ARGH^+)_8SiW_{18}Nb_6O_{77} \cdot 18H_2O$
$(LYSH^+)_7K\ SiW_{18}Nb_6O_{77} \cdot 18H_2O$
$(HISH^+)_6K_2\ SiW_{18}Nb_6O_{77} \cdot 18H_2O$
$H_8Si_2W_{18}Nb_6O_{77} \cdot nH_2O$ (2 batches)
$[(CH_3)_4N^+]_4SiW_{11}O_{39}\text{—}O(SiCH_2CH_3)_2$
$[(CH_3)_4N^+]_4SiW_{11}O_{39}\text{—}O(SiCH_3)_2$
$[(CH_3)_4N^+]_4SiW_{11}O_{39}\text{—}O(SiC_{16}H_{33})_2$
$Li_7HSi_2W_{18}Nb_6O_{77}$
$Li_9P_2V_3Me_3W_{12}O_{62}$
$Cs_9P_2V_3MeW_{12}O_{62}$
$Cs_{12}P_2V_3W_{12}O_{62}$
$K_4H_2PV_4W_8O_{40}$
$Na_{12}P_4W_{14}O_{58}$
$Na_{14}H_6P_6W_{18}O_{79}$
$a\text{-}K_5(Nb_{O2})SiW_{11}O_{39}$ $K_5(TaO_2)SiW_{11}O_{39}$
$(Me_3NH)_5(NbO_2)SiW_{11}O_{39}$
$(Me_3NH)_5NbSiW_{11}O_{40}$
$(Me_3NH)_5(TaO_2)SiW_{11}O_{39}$
$K_4(NbO_2)PW_{11}O_{39}$
$K_7(NbO_2)P_2W_{12}O_{61}$
$(Me_3NH)_7(NbO_2)_3SiW_9O_{37}$
$Cs_7(NbO_2)_3SiW_9O_{37}$
$K_6(NbO_2)_3PW_9O_{37}$
$Na_{10}(H_2W_{12}O_{42})$
$K_4NbPW_{11}O_{40}$
$(Me_3NH)_4NbPW_{11}O_{40}$
$K_5NbSiW_{11}O_{40}$
$K_5TaSiW_{11}O_{40}$
$(Me_3NH)_5TaSiW_{11}O_{40}$
$K_6Nb_3PW_9O_{40}$
$K_7NbP_2W_{17}O_{62}$
$K_7(TiO_2)_2PW_{10}O_{38}$
$K_7(TaO_2)_3SiW_9O_{37}$
$K_7Ta_3SiW_9O_{40}$
$K_6(TaO_2)_3PW_9O_{37}$
$K_6Ta_3PW_9O_{40}$
$K_8Co_2W_{11}O_{39}$
$H_2(Me_4N)_4(EtSi)_2CoW_{11}O_{40}$
$H_2(Me_4N)_4(iso-C_4H_9Si)_2CoW_{11}O_{40}$
$K_9(NbO_2)_3P_2W_{15}O_{59}$
$K_9Nb_3P_2W_{15}O_{62}$
$K_{12}(NbO_2)_6P_2W_{12}O_{56}$
$K_{12}Nb_6P_2W_{12}O_{62}$
$a_2-K_{10}P_2W_{17}O_{61}$
$K_6Fe(III)Nb_3P_2W_{15}O_{62}$
$K_7Zn(II)Nb_3P_2W_{15}O_{62}$
$(NH_4)_6[a-P_2W_{18}O_{62}] \cdot nH_2O$
$K_{12}[H_2P_2W_{12}O_{48}] \cdot 24H_2O$
$K_{12}[H_2P_2W_{12}O_{48}] \cdot 24H_2O$
$K_2Na_{1.5}H_{4.5}[PtMo_6O_{24}] \cdot 8H_2O$
$K_6[a_2-P_2W_{17}MoO_{62}] \cdot nH_2O$
$KHP_2V_3W_{15}O_{62} \cdot 34H_2O$
$K_6[P_2W_{12}Nb_6O_{62}] \cdot 24H_2O$
$Na_6[V_{10}O_{28}] \cdot 18H_2O$
$(Guanidinium)_8H[PV_{14}O_{62}] \cdot 3H_2O$
$K_8H[PV_{14}O_{62}]$
$Na_7[MnV_{13}O_{38}] \cdot 18H_2O$
$K_6[BW_{11}O_{39}Ga(OH_2)] \cdot 13H_2O$
$K_7H[Nb_6O_{19}] \cdot 13H_2O$
$K_7H[Nb_6O_{19}] \cdot 13H_2O$
$[MeN/Na/K]_4[Nb_2W_4O_{19}]$
$[Me_4N]_9[P_2W_{15}Nb_3P_{62}]$
$[Me_4N]_{15}[HP_4W_{30}Nb_6O_{123}] \cdot 16H_2O$
$[Me_4N]_{15}[HP_4W_{30}Nb_6O_{123}] \cdot 16H_2O$
$[Na/K]_6Nb_4W_2O_{19}]$
$[Me_4N/Na/K]_5[Nb_3W_3O_{19}] \cdot 6H_2O$
$[Me_4N/Na/K]_5[Nb_3W_3O_{19}] \cdot 6H_2O$
$[Me_5CpRh]_4V_6O_{19}]$
$K_5[CpTiSiW_{11}O_{39}] \cdot 12H_2O$
$b_2-K_8[SiW_{11}O_{39}] \cdot 14H_2O$
$a-K_8[SiW_{10}O_{36}] \cdot 12H_2O$
$Cs_7Na_2[PW_{10}O_{37}] \cdot 8H_2O$
$Cs_6[P_2W_5O_{23}] \cdot 7(½)H_2O$
$g-Cs_7[PW_{10}O_{36}] \cdot 7H_2O$
$K_5[SiNbW_{11}O_{40}] \cdot 7H_2O$
$K_4[PNbW_{11}O_{40}] \cdot 12H_2O$
$Na_6[Nb_4W_2O_{19}] \cdot 13H_2O$
$Na_6[Nb_4W_2O_{19}] \cdot 20H_2O$
$K_6[Nb_4W_2O_{19}] \cdot 7H_2O$
$K_4[V_2W_4O_{19}] \cdot 3.5H_2O$
$Na_5[V_3W_3O_{19}] \cdot 12H_2O$
$K_6[PV_3W_9O_{40}] \cdot 14H_2O$
$Na_9[A-b-GeW_9O_{34}] \cdot 8H_2O$
$Na_{10}[A-a-GeW_9O_{34}] \cdot 9H_2O$
$K_7[BV_2W_{10}O_{40}] \cdot 6H_2O$
$Na_5[CH_3Sn(Nb_6O_{19})] \cdot 10H_2O$
$Na_5[CH_3Sn(Nb_6O_{19})] \cdot 10H_2O$
$Na_8[Pt(P(m-SO_3Ph))_3Cl] \cdot 3H_2O$
$Na_3[P(m-SO_3Ph)_3] \cdot H_2O$
$(Me_3NH)_{10}(H)[Si_2(ZrOH)_3W_{18}O_{68}] \cdot 10H_2O$
$(Me_3NH)_{10}(H)[Si_2(ZrOH)_3W_{18}O_{68}] \cdot 10H_2O$
$K_7[A-a-GeNb_3W_9O_{40}] \cdot 18H_2O$
$K_7[A-b-SiNb_3W_9O_{40}] \cdot 20H_2O$
$(Me_3NH)_9[A-a-HSi_2Nb_6W_{18}O_{78}]$
$(Me_3NH)_9[A-a-HGe_2Nb_6W_{18}O_{78}]$
$(Me_3NH)_9[A-a-HGe_2Nb_6W_{18}O_{78}]$
$K_7(H)[A-a-Ge_2Nb_6W_{18}O_{77}] \cdot 18H_2O$
$K_8[A-b-Si_2Nb_6W_{18}O_{77}]$ and
$(Me_3NH)_8[A-b-Si_2Nb_6W_{18}O_{77}]$.

11. The method of claim 10, wherein said hepadnavirus is hepatitis B virus.

12. The method of claim 10, wherein said polyoxometalate is $K_8(A-\beta-Si_2Nb_6W_{18}O_{77})$.

* * * * *